US012691050B2

(12) United States Patent
Cavaco Paulo et al.

(10) Patent No.: US 12,691,050 B2
(45) Date of Patent: *Jul. 28, 2026

(54) FRAGRANCE RELEASE MECHANISM, METHOD AND USES THEREOF

(71) Applicant: Universidade do Minho, Braga (PT)

(72) Inventors: Artur Manuel Cavaco Paulo, Braga (PT); Filipa Daniela Gomes Gonçalves, Braga (PT); Artur Jorge Araújo Magalhães Ribeiro, Braga (PT); Carla Manuela Pereira Marinho Da Silva, Guimaraes (PT)

(73) Assignee: UNIVERSIDADE DO MINHO, Braga (PT)

( * ) Notice: Subject to any disclaimer, the term of this patent is extended or adjusted under 35 U.S.C. 154(b) by 190 days.

This patent is subject to a terminal disclaimer.

(21) Appl. No.: 18/003,127

(22) PCT Filed: Jul. 5, 2021

(86) PCT No.: PCT/IB2021/056011
§ 371 (c)(1),
(2) Date: Dec. 22, 2022

(87) PCT Pub. No.: WO2022/003655
PCT Pub. Date: Jan. 6, 2022

(65) Prior Publication Data
US 2023/0248631 A1 Aug. 10, 2023

(30) Foreign Application Priority Data

Jul. 3, 2020 (PT) .......................................... 116561
Nov. 6, 2020 (EP) ..................................... 20206292

(51) Int. Cl.
A61K 38/00 (2006.01)
A61K 8/11 (2006.01)
A61K 8/64 (2006.01)
A61Q 15/00 (2006.01)
C07K 14/00 (2006.01)

(52) U.S. Cl.
CPC .................. *A61K 8/64* (2013.01); *A61K 8/11* (2013.01); *A61Q 15/00* (2013.01)

(58) Field of Classification Search
CPC . A61K 8/11; A61K 8/64; A61K 38/00; A61Q 15/00; C07K 14/00
See application file for complete search history.

(56) References Cited

U.S. PATENT DOCUMENTS

| | | | |
|---|---|---|---|
| 5,028,419 A | 7/1991 | Pigiet | |
| 5,635,170 A | 6/1997 | Lang et al. | |
| 6,020,163 A * | 2/2000 | Conklin ................. | C07K 14/47 435/320.1 |
| 7,622,273 B2 * | 11/2009 | Gibbs ...................... | C12Q 1/34 435/23 |
| 7,919,456 B2 * | 4/2011 | Ghosh .................... | A61K 35/32 514/16.8 |
| 8,034,338 B2 * | 10/2011 | Loibner .................. | A61P 39/00 435/69.6 |
| 8,383,580 B2 | 2/2013 | Rui et al. | |
| 8,809,259 B2 | 8/2014 | Berry et al. | |
| 9,713,604 B2 | 7/2017 | Dreher | |
| 10,709,655 B2 | 7/2020 | Cavaco Paulo et al. | |
| 11,642,298 B2 | 5/2023 | Cavaco Paulo et al. | |
| 11,712,410 B2 | 8/2023 | Sahib et al. | |
| 12,102,706 B2 | 10/2024 | Cavaco Paulo | |
| 12,115,242 B2 | 10/2024 | Cavaco Paulo | |
| 2006/0272103 A1 | 12/2006 | Barbarat | |
| 2006/0286655 A1 | 12/2006 | Philippe | |
| 2008/0107614 A1 | 5/2008 | Fahnestock et al. | |
| 2008/0317691 A1 | 12/2008 | Huang et al. | |
| 2010/0015070 A1 | 1/2010 | Bollschweiler et al. | |
| 2010/0272666 A1 | 10/2010 | Breakspear et al. | |
| 2012/0087862 A1 * | 4/2012 | Hood ................. | G01N 33/6845 424/9.1 |
| 2013/0059772 A1 | 3/2013 | Kumar | |
| 2013/0224269 A1 | 8/2013 | Khan et al. | |
| 2016/0271043 A1 | 9/2016 | Cavaco Paulo et al. | |
| 2020/0121581 A1 | 4/2020 | Shoseyov et al. | |
| 2021/0393500 A1 | 12/2021 | Cavaco Paulo et al. | |
| 2022/0151977 A1 | 5/2022 | Berry | |
| 2022/0287944 A1 | 9/2022 | Costache et al. | |
| 2023/0248627 A1 | 8/2023 | Cavaco Paulo et al. | |
| 2023/0301894 A1 | 9/2023 | Cavaco Paulo et al. | |
| 2023/0338263 A1 | 10/2023 | Cavaco Paulo et al. | |
| 2023/0355499 A1 | 11/2023 | Sahib et al. | |

(Continued)

FOREIGN PATENT DOCUMENTS

| | | |
|---|---|---|
| CN | 103126949 A | 6/2013 |
| CN | 104940071 A | 9/2015 |

(Continued)

OTHER PUBLICATIONS

BLAST glossary downloaded from www.ncbi.nlm.nih.gov on May 2, 2020.
BLAST search for SEQ ID No. 1, downloaded May 2, 2020 (2020).
BLAST search for SEQ ID No. 2, downloaded May 2, 2020 (2020).
Co-pending U.S. Appl. No. 18/252,712, inventors Cavaco; Paulo Artur Manuel et al., filed May 11, 2023.
Co-pending U.S. Appl. No. 18/339,889, inventors Cavaco; Paulo Artur Manuel et al., filed Jun. 22, 2023.
Co-pending U.S. Appl. No. 18/339,927, inventors Cavaco; Paulo Artur Manuel et al., filed Jun. 22, 2023.

(Continued)

*Primary Examiner* — Julie Ha
(74) *Attorney, Agent, or Firm* — Leason Ellis LLP

(57) ABSTRACT

A release composition comprising a protein and an active agent, wherein the active agent is released when in presence of an electrolyte solution is described. A kit and an article comprising the release composition of the present-subject matter are also encompassed.

16 Claims, 1 Drawing Sheet
Specification includes a Sequence Listing.

(56) References Cited

U.S. PATENT DOCUMENTS

| | | |
|---|---|---|
| 2023/0414478 A1 | 12/2023 | Cavaco Paulo |
| 2023/0414479 A1 | 12/2023 | Cavaco Paulo |
| 2023/0415070 A1 | 12/2023 | Cavaco Paulo |
| 2024/0082135 A1 | 3/2024 | Cavaco Paulo |
| 2024/0108560 A1 | 4/2024 | Staley |
| 2024/0115481 A1 | 4/2024 | Cavaco Paulo et al. |
| 2024/0316187 A1 | 9/2024 | Von Mutius |

FOREIGN PATENT DOCUMENTS

| | | |
|---|---|---|
| EP | 0335654 A2 | 10/1989 |
| EP | 0488242 A1 | 6/1992 |
| EP | 1705188 A1 | 9/2006 |
| FR | 2706300 A1 | 12/1994 |
| FR | 2797447 B1 | 4/2004 |
| FR | 2876286 A1 | 4/2006 |
| GB | 103484 A | 1/1918 |
| JP | H0656889 A | 3/1994 |
| JP | H1112138 A | 1/1999 |
| JP | 2005151849 A | 6/2005 |
| PT | 103484 A | 11/2007 |
| WO | WO-9711672 A1 | 4/1997 |
| WO | WO-0023039 A2 | 4/2000 |
| WO | WO-0051556 A1 | 9/2000 |
| WO | WO-0064405 A2 | 11/2000 |
| WO | WO-0112806 A2 | 2/2001 |
| WO | WO-0123890 A1 | 4/2001 |
| WO | WO-2004048399 A2 | 6/2004 |
| WO | WO-2005049834 A1 | 6/2005 |
| WO | WO-2006001536 A1 | 1/2006 |
| WO | WO-2007136286 A1 | 11/2007 |
| WO | WO-2008081348 A2 | 7/2008 |
| WO | WO-2010010145 A1 | 1/2010 |
| WO | WO-2011072991 A1 | 6/2011 |
| WO | WO-2012013593 A1 | 2/2012 |
| WO | WO-2015056216 A2 | 4/2015 |
| WO | WO-2022003655 A1 | 1/2022 |
| WO | WO-2023081711 A1 | 5/2023 |
| WO | WO-2024073683 A2 | 4/2024 |
| WO | 2024206473 A1 | 10/2024 |

OTHER PUBLICATIONS

Co-pending U.S. Appl. No. 18/478,320, inventors Staley; Karis et al., filed Sep. 29, 2023.

Co-pending U.S. Appl. No. 18/497,900, inventors Cavaco Paulo; Arthur Manuel et al., filed Oct. 30, 2023.

Co-pending U.S. Appl. No. 18/520,428, inventors Cavaco Paulo; Artur Manuel et al., filed Nov. 27, 2023.

Dow, Carbowax Sentry Polyethylene Glycols, published online 2011.

Fernanda Reis Gavazzoni Dias. Hair Cosmetics: An Overview. International Journal of Trichology 7:2-15 (2015).

Fernandes et al. Keratin-based peptide: biological evaluation and strengthening properties on relaxed hair. International Journal of Cosmetic Science 34(4):338-346 (2012).

Koonin et al. Chapter 2 Evolutionary Concept in Genetics and Genomics. MY. Sequence—Evolution—Function: Computational Approaches in Comparative Genomics. Boston: Kluwer Academic. Available from: https:// www.ncbi.nlnn.nih.gov/books/NBK20260/ (pp. 3 ) (2003).

Marabotti et al. The misuse of terms in scientific literature. Bioinformatics 26(19):2498 (2010).

Naturally Curly, http://www.naturallycurly.com/curlreading/kinky-hair-type-4a/ingredients-commonly-used-in-hair-care-productspeg-modified-materials/, published online Jun. 8, 2010.

PCT/IB2014/065375 International Search Report and Written Opinion dated Jun. 7, 2015.

Romanowski. An introduction to cosmetic technology. American Oil Chemists' Society. Available at https://www.aocs.org/stay-informed/inform-magazine/featured-articles/an-introduction-to-cosmetic-technology-april-2015?SSO=True (8 pgs.) (2015).

Shimomura et al. Human Hair Keratin-Associated Proteins. J Investig Dermatol Symp Proc 10:230-233 (2005).

Thesis from Celia Freitas Da Cruz, Unraveling and modulating human hair morphology features (192 pgs) (2012).

Uniprot Protein Database, protein accession A8MUX0 , Keratin-associated protein 16-1, accessed on Dec. 18, 2019.

Uniprot Protein Database, protein accession P26371 , Keratin-associated protein 5-9, accessed on Dec. 18, 2019.

Uniprot Protein Database, protein accession Q9NSB0, Type II hair keratin 6, accessed on Dec. 18, 2019.

Uniprot Protein Database, protein Accession Q9NSB5, accessed on Nov. 8, 2019.

Uniprot protein database, protein Type II hair keratin 1, protein accession Q9NSB5, accessed on Aug. 28, 2017.

U.S. Forest Service entry on soaps at www.fs.fed.us/wildflowers/ethnobotany/soaps.shtra, downloaded Sep. 29, 2020 (2020).

U.S. Appl. No. 15/030,313 Office Action dated Aug. 29, 2018.

U.S. Appl. No. 15/030,313 Office Action dated Aug. 31, 2017.

U.S. Appl. No. 15/030,313 Office Action dated Jan. 11, 2019.

U.S. Appl. No. 15/030,313 Office Action dated Jan. 24, 2018.

U.S. Appl. No. 15/030,313 Office Action dated Jul. 18, 2019.

U.S. Appl. No. 15/030,313 Office Action dated Mar. 2, 2017.

U.S. Appl. No. 16/122,796 Office Action dated Apr. 15, 2021.

U.S. Appl. No. 16/122,796 Office Action dated Apr. 28, 2023.

U.S. Appl. No. 16/122,796 Office Action dated Jan. 5, 2023.

U.S. Appl. No. 16/122,796 Office Action dated May 4, 2020.

U.S. Appl. No. 16/122,796 Office Action dated Oct. 1, 2020.

U.S. Appl. No. 16/122,796 Office Action dated Sep. 20, 2022.

U.S. Appl. No. 16/439,889 Office Action dated Apr. 1, 2022.

U.S. Appl. No. 16/439,889 Office Action dated Jan. 3, 2020.

U.S. Appl. No. 16/439,889 Office Action dated Sep. 15, 2022.

U.S. Appl. No. 18/164,515 Office Action dated Oct. 12, 2023.

U.S. Appl. No. 18/334,287 Office Action dated Oct. 10, 2023.

Yang. Chapter 36: Hair Care Cosmetics. Cosmetic Science and Technology: Theoretical Principles and Applications (pp. 601-615) (2017).

Castro et al. The Structural Properties of Odorants Modulate Their Association to Human Odorant Binding Protein. Biomolecules 11(2):145 (2021).

Berendsen, HJ., A glimpse of the Holy Grail? Science 282(5389):642-643 (1998).

Bradley et al. Limits of cooperativity in a structurally modular protein: response of the Notch ankyrin domain to analogous alanine substitutions in each repeat. J Mol Biol. 324(2):373-386 (2002).

CN104940071A English Translation Published: Sep. 30, 2015.

EP1238645A2 English Translation Published: Sep. 11, 2002.

Ngo, Thomas, et al., Computational Complexity, Protein Structure Prediction, and the Levinthal Paradox. Birkhauser Boston 491-495 (1994).

Rudinger, J., Characteristics of the amino acids as components of a peptide hormone sequence. Peptide Hormones, J.A, Parsons , MA, BM, BCh, 1-7 (1976).

Schinzel, R, et al., The Phosphate Recognition Site of *Escherichia coli* Maltodextrin Phosphorylase. FEBS Letters 286(1-2):125-128 (1991).

Sigma, Designing Custom Peptides, pp. 1-2. (2004).

SOLU Shampoo. https://web.archive.Org/web/20200929001233/ https://www.thekindestcut.com/product-page/solu-shampoo. Published: Sep. 29, 2020.

U.S. Appl. No. 18/339,927 Office Action dated May 8, 2024.

U.S. Appl. No. 18/520,428 Office Action dated Mar. 25, 2024.

Voet, Judith., Biochemistry, Second Edition, John Wiley & Sons, Inc., 235-241 (1995).

Yampolsky, Lev, et al., The Exchangeability of Amino Acids in Proteins. Genetics 170(4):1459-1472 (2005).

Altschul et al., Basic Local Alignment Search Tool. J. Mol. Biol. 215:403-410 (1990).

Archunan. Odorant Binding Proteins: a key player in the sense of smell. Bioinformation 14(1):36-37 (2018).

Bignetti et al. Purification and characterisation of an odorant-binding protein from cow nasal tissue. Eur. J. Biochem. 149:227-231 (1985).

(56) References Cited

OTHER PUBLICATIONS

Bignetti et al. The pyrazine-binding protein and olfaction. Comp. Biochem. Physiol., 90(1):1-5 (1988).

Breer. Olfactory receptors: molecular basis for recognition and discrimination of odors. Anal Bioanal Chem 377(3):427-33 (2003).

Briand et al. Evidence of an Odorant-Binding Protein in the Human Olfactory Mucus: Location, Structural Characterization, and Odorant-Binding Properties. Biochemistry 41:7241-7252 (2002).

Campanella et al., MatGAT: An application that generates similarity/identity matrices using protein or DNA sequences. BMC Bioinformatics 4:29 (2003).

Capo et al. The porcine odorant-binding protein as molecular probe for benzene detection. PloS One 13(9):e0202630 (2018).

Cave et al. Progress in the development of olfactory-based bioelectronic chemosensors. Biosens Bioelectron 123:211-222 (2019).

Cennamo et al. Easy to Use Plastic Optical Fiber-Based Biosensor for Detection of Butanal. PloS One 10(3):e0116770 (2015).

Dal Monte et al. Purification and characterization of two odorant-binding proteins from nasal tisue of rabbit and pig. Comp Biochem Physiol 99(2):445-451 (1991).

Di Pietrantonio et al. Detection of odorant molecules via surface acoustic wave biosensor array based on odorant-binding proteins. Biosens Bioelectron 41:328-34 (2013).

Flower. Beyond the superfamily: the lipocalin receptors. Biochim Biophys Acta 1482:327-336 (2000).

Flower. The lipocalin protein family : structure and function. Biochem. J. 318(Pt 1)(Pt 1):1-14 (1996).

Garibotti et al. Three Odorant-binding Proteins from Rabbit Nasal Mucosa. Chem Senses 22(4):383-390 (1997).

Goncalves et al. OBP fused with cell-penetrating peptides promotes liposomal transduction. Colloids Surf B Biointerfaces 161:645-653 (2018).

Goncalves et al. Release of Fragrances from Cotton Functionalized with Carbohydrate-Binding Module Proteins. ACS Applied Mater Interfaces 11(31):28499-28506 (2019).

Goncalves et al. Two Engineered OBPs with opposite temperature-dependent affinities towards 1-aminoanthracene. Sci Rep 8 (1):14844 (2018).

Gongalves et al. 1-Aminoanthracene Transduction into Liposomes Driven by Odorant-Binding Protein Proximity. ACS Applied Mater Interfaces 10(32):27531-27539 (2018).

Han et al. Operating Mechanism and Molecular Dynamics of Pheromone-Binding Protein ASP1 as Influenced by pH. PLoS One 9(10):e110565 (2014).

Kozlowski. IPC—Isoelectric Point Calculator. Biol Direct 11(1):55 (2016).

Lazar et al. Molecular and Functional Characterization of an Odorant Binding Protein of the Asian Elephant, Elephas maximus: Implications for the Role of Lipocalins in Mammalian Olfaction. Biochemistry 41:11786-11794 (2002).

Lobel et al. Odorant of different chemical classes interact with distinct odorant binding protein subtypes. Chem Senses 27:39-44 (2002).

Malpeli et al. Chapter 9: Purification and Fluorescent Titration of Cellular Retinol-Binding Protein. In Methods in Molecular Biology; Redfern, C. P. F., Ed.; pp. 111-122 (1998).

Mazzini et al. Dissociation and unfolding of bovine odorant binding protein at acidic pH. J Struct Biol 159(1):82-91 (2007).

Mulla et al. Capacitance-modulated transistor detects odorant binding protein chiral interactions. Nature Commun 6:6010 (2015).

Needleman et al. A general method applicable to the search for similarities in the amino acid sequence of two proteins. J. Mol. Biol. 48:443-453 (1970).

Nogueira et al. Peptide anchor for folate-targeted liposomal delivery. Biomacromolecules 16(9):2904-2910 (2015).

Ozeki et al. A study of the suppression of body odour in elderly subjects by anti-fungal agents. Int J Cosmet Sci 38(3):312-8 (2016).

Paolini et al. Porcine odorant-binding protein: structural stability and ligand affinities measured by Fourier-transform infrared spectroscopy and fluorescence spectroscopy. Biochim Biophys Acta 1431:179-188 (1999).

Parisi et al. Unfolding and refolding of porcine odorant binding protein in guanidinium hydrochloride: equilibrium studies at neutral pH. Biochim Biophys Acta 652(2):115-125 (2003).

PCT/IB2021/056011 International Search Report and Written Opinion dated Oct. 6, 2021.

Pelosi et al. Odorant-Binding Proteins as Sensing Elements for Odour Monitoring. Sensors (Basel) 18(10):3248 (2018).

Pelosi et al. Structure and biotechnological applications of odorant-binding proteins. Appl Microbiol Biotechnol 98(1):61-70 (2014).

Pelosi. Odorant-Binding Proteins: Structural Aspects. In Annals New York academy of sciences; Olfaction and Taste XII: an international symposium, pp. 281-293 (1998).

Perduca et al. Crystal Structure of a Truncated Form of Porcine Odorant-Binding Protein. Proteins 42:201-209 (2001).

Pes et al. Isolation of two odorant-binding proteins from mouse nasal tissue. Comp. Biochem. Physiol. 103 (4):1011-1017 (1992).

Pevsner et al. Odorant-binding protein: characterization of ligand binding. J Biol Chem 265(11):6118-6125 (1990).

Sankaran et al. Biology and applications of olfactory sensing system: A review. Sensors and Actuators B: Chemical 171-172:1-17 (2012).

Silva et al. Odorant binding proteins: a biotechnological tool for odour control. Appl Microbiol Biotechnol 98(8):3629-3638 (2014).

Sorokowska et al. Does Personality Smell? Accuracy of Personality Assessments Based on Body Odour. European Journal of Personality 26(5):496-503 (2012).

Spinelli et al. The Structure of the Monomeric Porcine Odorant Binding Protein Sheds Light on the Domain Swapping Mechanism. Biochemistry 37:7913-7918 (1998).

Tegoni et al. Mammalian odorant binding proteins. Biochim Biophys Acta 1482:229-240 (2000).

Vincent et al. Crystal structures of bovine odorant-binding protein in complex with odorant molecules. Eur J Biochem 271(19):3832-42 (2004).

Whitson et al. Human Odorant Binding Protein 2a has Two Affinity States and is Capable of Binding Some Uremic Toxins. Biochem Anal Biochem 3:2 (2014).

Chen et al., "Progress in the Development of Detection Strategies Based on Olfactory and Gustatory Biomimetic Biosensors", biosensors, Oct. 2022, pp. 1-40.

El Kazzy et al., "Study and optimization of the selectivity of an odorant binding protein-based bioelectronic nose", Biosensors and Bioelectronics, Oct. 2024, pp. 1-9.

Gonçalves et al., "Odorant-binding protein as active ingredient for fragrance release regulated by sweat", International Journal of Biological Macromolecules, Jan. 2026, pp. 1-10.

Ha et al., "Cellular andMolecular Roles of Human Odorant-Binding Proteins and Related Lipocalins in Olfaction and Neuroinflammation", cells, Nov. 2025, pp. 1-25.

Lalis et al., "How allosteric mutations control ligand binding in Lipocalin protein:odorant binding protein as a test case", Cellular and Molecular Sciences, Jun. 2025, pp. 1-14.

Moitrier et al., "Ligand Binding Properties of Odorant-Binding Protein OBP5 from Mus musculus", biology, Dec. 2022, pp. 1-13.

Nakanishi et al., "OBP2A regulates epidermal barrier function and protects against cytotoxic small hydrophobic molecules", Nov. 2024, pp. 1-20.

Paesani et al., "Odorant Binding Proteins Facilitate the Gas-Phase Uptake of Odorants Through the Nasal Mucus", Chemistry—A European Journal, Jan. 2025, pp. 1-9.

Vincent et al., "Crystal structures of bovine odorant-binding protein in complex with odorant molecules", Eur J. Biochem, Jul. 2004, pp. 3832-3842.

Brito et al. "Current and potential biotechnological applications of odorantbinding proteins", Appl. Microbiol. Biotechnol., Sep. 2020 (18 pages).

Hellman, " Stability of OBPs", Chapter Nine, Methods in Enzymology, Jan. 2020, pp. 193-228.

(56)        References Cited

OTHER PUBLICATIONS

No Author, "odorant binding protein [Sus scrofa]", https://www.ncbi.nlm.nih.gov/protein/AAL31550.1/, retrieved Feb. 18, 2026 (1 page).

Rusina et al., "Olfaction: From Nose to Brain, Stumbling and Falling", https://biomolecula.ru/articles/obonianie-ot-nosa-k-mozgu-spotykaias-i-padaia#source-61, Feb. 2021 (69 pages).

* cited by examiner

A
B
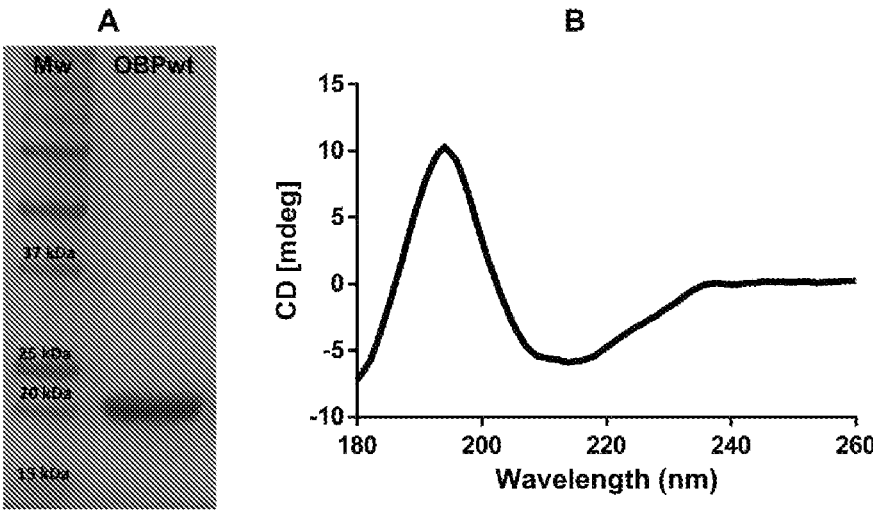

SEQUENCE LISTING

```
<160> NUMBER OF SEQ ID NOS: 22

<210> SEQ ID NO 1
<211> LENGTH: 157
<212> TYPE: PRT
<213> ORGANISM: Sus scrofa domesticus
<220> FEATURE:
<223> OTHER INFORMATION: Pig OBP (PDB ID 1DZK)

<400> SEQUENCE: 1

Gln Glu Pro Gln Pro Glu Gln Asp Pro Phe Glu Leu Ser Gly Lys Trp
1               5                   10                  15
```

-continued

```
Ile Thr Ser Tyr Ile Gly Ser Ser Asp Leu Glu Lys Ile Gly Glu Asn
            20                  25                  30

Ala Pro Phe Gln Val Phe Met Arg Ser Ile Glu Phe Asp Asp Lys Glu
        35                  40                  45

Ser Lys Val Tyr Leu Asn Phe Phe Ser Lys Glu Asn Gly Ile Cys Glu
    50                  55                  60

Glu Phe Ser Leu Ile Gly Thr Lys Gln Glu Gly Asn Thr Tyr Asp Val
65                  70                  75                  80

Asn Tyr Ala Gly Asn Asn Lys Phe Val Val Ser Tyr Ala Ser Glu Thr
                85                  90                  95

Ala Leu Ile Ile Ser Asn Ile Asn Val Asp Glu Glu Gly Asp Lys Thr
            100                 105                 110

Ile Met Thr Gly Leu Leu Gly Lys Gly Thr Asp Ile Glu Asp Gln Asp
            115                 120                 125

Leu Glu Lys Phe Lys Glu Val Thr Arg Glu Asn Gly Ile Pro Glu Glu
    130                 135                 140

Asn Ile Val Asn Ile Ile Glu Arg Asp Asp Cys Pro Ala
145                 150                 155
```

```
<210> SEQ ID NO 2
<211> LENGTH: 170
<212> TYPE: PRT
<213> ORGANISM: Homo sapiens
<220> FEATURE:
<223> OTHER INFORMATION: Human OBPIIa (UniProt ID Q9NY56)

<400> SEQUENCE: 2
```

```
Met Lys Thr Leu Phe Leu Gly Val Thr Leu Gly Leu Ala Ala Ala Leu
1               5                   10                  15

Ser Phe Thr Leu Glu Glu Glu Asp Ile Thr Gly Thr Trp Tyr Val Lys
            20                  25                  30

Ala Met Val Val Asp Lys Asp Phe Pro Glu Asp Arg Arg Pro Arg Lys
        35                  40                  45

Val Ser Pro Val Lys Val Thr Ala Leu Gly Gly Gly Asn Leu Glu Ala
    50                  55                  60

Thr Phe Thr Phe Met Arg Glu Asp Arg Cys Ile Gln Lys Lys Ile Leu
65                  70                  75                  80

Met Arg Lys Thr Glu Glu Pro Gly Lys Phe Ser Ala Tyr Gly Gly Arg
                85                  90                  95

Lys Leu Ile Tyr Leu Gln Glu Leu Pro Gly Thr Asp Asp Tyr Val Phe
            100                 105                 110

Tyr Cys Lys Asp Gln Arg Arg Gly Gly Leu Arg Tyr Met Gly Lys Leu
            115                 120                 125

Val Gly Arg Asn Pro Asn Thr Asn Leu Glu Ala Leu Glu Glu Phe Lys
    130                 135                 140

Lys Leu Val Gln His Lys Gly Leu Ser Glu Glu Asp Ile Phe Met Pro
145                 150                 155                 160

Leu Gln Thr Gly Ser Cys Val Leu Glu His
                165                 170
```

```
<210> SEQ ID NO 3
<211> LENGTH: 170
<212> TYPE: PRT
<213> ORGANISM: Homo sapiens
<220> FEATURE:
<223> OTHER INFORMATION: Human OBPIIb (UniProt ID Q9NPH6)

<400> SEQUENCE: 3
```

```
Met Lys Thr Leu Phe Leu Gly Val Thr Leu Gly Leu Ala Ala Ala Leu
1               5                   10                  15

Ser Phe Thr Leu Glu Glu Glu Asp Ile Thr Gly Thr Trp Tyr Val Lys
                20                  25                  30

Ala Met Val Val Asp Lys Asp Phe Pro Glu Asp Arg Arg Pro Arg Lys
        35                  40                  45

Val Ser Pro Val Lys Val Thr Ala Leu Gly Gly Gly Lys Leu Glu Ala
    50                  55                  60

Thr Phe Thr Phe Met Arg Glu Asp Arg Cys Ile Gln Lys Lys Ile Leu
65                  70                  75                  80

Met Arg Lys Thr Glu Glu Pro Gly Lys Tyr Ser Ala Tyr Gly Gly Arg
                85                  90                  95

Lys Leu Met Tyr Leu Gln Glu Leu Pro Arg Arg Asp His Tyr Ile Phe
            100                 105                 110

Tyr Cys Lys Asp Gln His His Gly Gly Leu Leu His Met Gly Lys Leu
        115                 120                 125

Val Gly Arg Asn Ser Asp Thr Asn Arg Glu Ala Leu Glu Glu Phe Lys
    130                 135                 140

Lys Leu Val Gln Arg Lys Gly Leu Ser Glu Glu Asp Ile Phe Thr Pro
145                 150                 155                 160

Leu Gln Thr Gly Ser Cys Val Pro Glu His
                165                 170
```

```
<210> SEQ ID NO 4
<211> LENGTH: 163
<212> TYPE: PRT
<213> ORGANISM: Mus musculus
<220> FEATURE:
<223> OTHER INFORMATION: Mouse OBP (UniProt ID OBP1A)

<400> SEQUENCE: 4
```

```
Met Ala Lys Phe Leu Leu Leu Ala Leu Thr Phe Gly Leu Ala His Ala
1               5                   10                  15

Ala Met Glu Gly Pro Trp Lys Thr Val Ala Ile Ala Ala Asp Arg Val
                20                  25                  30

Asp Lys Ile Glu Arg Gly Gly Glu Leu Arg Ile Tyr Cys Arg Ser Leu
        35                  40                  45

Thr Cys Glu Lys Glu Cys Lys Glu Met Lys Val Thr Phe Tyr Val Asn
    50                  55                  60

Glu Asn Gly Gln Cys Ser Leu Thr Thr Ile Thr Gly Tyr Leu Gln Glu
65                  70                  75                  80

Asp Gly Lys Thr Tyr Lys Thr Gln Phe Gln Gly Asn Asn Arg Tyr Lys
                85                  90                  95

Leu Val Asp Glu Ser Pro Glu Asn Leu Thr Phe Tyr Ser Glu Asn Val
            100                 105                 110

Asp Arg Ala Asp Arg Lys Thr Lys Leu Leu Phe Ile Leu Gly His Gly
        115                 120                 125

Pro Leu Thr Ser Glu Gln Lys Glu Lys Phe Ala Glu Leu Ala Glu Glu
    130                 135                 140

Lys Gly Ile Pro Ala Gly Asn Ile Arg Glu Val Leu Ile Thr Asp Tyr
145                 150                 155                 160

Cys Pro Glu
```

```
<210> SEQ ID NO 5
<211> LENGTH: 176
```

```
<212> TYPE: PRT
<213> ORGANISM: Mus musculus
<220> FEATURE:
<223> OTHER INFORMATION: Mouse OBP2A (UniProt ID Q8K1H9)

<400> SEQUENCE: 5

Met Lys Ser Leu Leu Leu Thr Ile Leu Leu Leu Gly Leu Val Ala Val
1               5                   10                  15

Leu Lys Ala Gln Glu Ala Pro Pro Asp Asp Leu Val Asp Tyr Ser Gly
                20                  25                  30

Ile Trp Tyr Ala Lys Ala Met Val His Asn Gly Thr Leu Pro Ser His
            35                  40                  45

Lys Ile Pro Ser Ile Val Phe Pro Val Arg Ile Ile Ala Leu Glu Glu
        50                  55                  60

Gly Asp Leu Glu Thr Thr Val Val Phe Trp Asn Asn Gly His Cys Arg
65                  70                  75                  80

Glu Phe Lys Phe Val Met Lys Lys Thr Glu Glu Pro Gly Lys Tyr Thr
                85                  90                  95

Ala Phe His Asn Thr Lys Val Ile His Val Glu Lys Thr Ser Val Asn
            100                 105                 110

Glu His Tyr Ile Phe Tyr Cys Glu Gly Arg His Asn Gly Thr Ser Ser
        115                 120                 125

Phe Gly Met Gly Lys Leu Met Gly Arg Asp Ser Gly Glu Asn Pro Glu
        130                 135                 140

Ala Met Glu Glu Phe Lys Asn Phe Ile Lys Arg Met Asn Leu Arg Leu
145                 150                 155                 160

Glu Asn Met Phe Val Pro Glu Ile Gly Asp Lys Cys Val Glu Ser Asp
                165                 170                 175

<210> SEQ ID NO 6
<211> LENGTH: 171
<212> TYPE: PRT
<213> ORGANISM: Mus musculus
<220> FEATURE:
<223> OTHER INFORMATION: Mouse OBP1B (UniProt ID A2AEP0)

<400> SEQUENCE: 6

Met Met Val Lys Phe Leu Leu Leu Ala Leu Val Phe Gly Leu Ala His
1               5                   10                  15

Val His Ala His Asp His Pro Glu Leu Gln Gly Gln Trp Lys Thr Thr
                20                  25                  30

Ala Ile Met Ala Asp Asn Ile Asp Lys Ile Glu Thr Ser Gly Pro Leu
            35                  40                  45

Glu Leu Phe Val Arg Glu Ile Thr Cys Asp Glu Gly Cys Gln Lys Met
        50                  55                  60

Lys Val Thr Phe Tyr Val Lys Gln Asn Gly Gln Cys Ser Leu Thr Thr
65                  70                  75                  80

Val Thr Gly Tyr Lys Gln Glu Asp Gly Lys Thr Phe Lys Asn Gln Tyr
                85                  90                  95

Glu Gly Glu Asn Asn Tyr Lys Leu Leu Lys Ala Thr Ser Glu Asn Leu
            100                 105                 110

Val Phe Tyr Asp Glu Asn Val Asp Arg Ala Ser Arg Lys Thr Lys Leu
        115                 120                 125

Leu Tyr Ile Leu Gly Lys Gly Glu Ala Leu Thr His Glu Gln Lys Glu
        130                 135                 140

Arg Leu Thr Glu Leu Ala Thr Gln Lys Gly Ile Pro Ala Gly Asn Leu
145                 150                 155                 160
```

Arg Glu Leu Ala His Glu Asp Thr Cys Pro Glu
            165                 170

<210> SEQ ID NO 7
<211> LENGTH: 157
<212> TYPE: PRT
<213> ORGANISM: Rattus rattus
<220> FEATURE:
<223> OTHER INFORMATION: Rat OBP (PDB ID 3FIQ)

<400> SEQUENCE: 7

His His Glu Asn Leu Asp Ile Ser Pro Ser Glu Val Asn Gly Asp Trp
1               5                   10                  15

Arg Thr Leu Tyr Ile Val Ala Asp Asn Val Glu Lys Val Ala Glu Gly
            20                  25                  30

Gly Ser Leu Arg Ala Tyr Phe Gln His Met Glu Cys Gly Asp Glu Cys
            35                  40                  45

Gln Glu Leu Lys Ile Ile Phe Asn Val Lys Leu Asp Ser Glu Cys Gln
        50                  55                  60

Thr His Thr Val Val Gly Gln Lys His Glu Asp Gly Arg Tyr Thr Thr
65                  70                  75                  80

Asp Tyr Ser Gly Arg Asn Tyr Phe His Val Leu Lys Lys Thr Asp Asp
                85                  90                  95

Ile Ile Phe Phe His Asn Val Asn Val Asp Glu Ser Gly Lys Glu Thr
            100                 105                 110

Asn Val Ile Leu Val Ala Gly Lys Arg Glu Asp Leu Asn Lys Ala Gln
            115                 120                 125

Lys Gln Glu Leu Arg Lys Leu Ala Glu Glu Tyr Asn Ile Pro Asn Glu
        130                 135                 140

Asn Thr Gln His Leu Val Pro Thr Asp Thr Cys Asn Gln
145                 150                 155

<210> SEQ ID NO 8
<211> LENGTH: 173
<212> TYPE: PRT
<213> ORGANISM: Rattus rattus
<220> FEATURE:
<223> OTHER INFORMATION: Rat OBP (PDB ID 3ZQ3)

<400> SEQUENCE: 8

Met Arg Gly Ser His His His His His His Thr Asp Pro Glu Glu Ala
1               5                   10                  15

Ser Phe Glu Arg Gly Asn Leu Asp Val Asp Lys Leu Asn Gly Asp Trp
            20                  25                  30

Phe Ser Ile Val Val Ala Ser Asp Lys Arg Glu Lys Ile Glu Glu Asn
            35                  40                  45

Gly Ser Met Arg Val Phe Val Gln His Ile Asp Val Leu Glu Asn Ser
        50                  55                  60

Leu Gly Phe Thr Phe Arg Ile Lys Glu Asn Gly Val Cys Thr Glu Phe
65                  70                  75                  80

Ser Leu Val Ala Asp Lys Thr Ala Lys Asp Gly Glu Tyr Phe Val Glu
                85                  90                  95

Tyr Asp Gly Glu Asn Thr Phe Thr Ile Leu Lys Thr Asp Tyr Asp Asn
            100                 105                 110

Tyr Val Met Phe His Leu Val Asn Val Asn Asn Gly Glu Thr Phe Gln
            115                 120                 125

Leu Met Glu Leu Tyr Gly Arg Thr Lys Asp Leu Ser Ser Asp Ile Lys

-continued

```
                 130                 135                 140

Glu Lys Phe Ala Lys Leu Cys Val Ala His Gly Ile Thr Arg Asp Asn
145                 150                 155                 160

Ile Ile Asp Leu Thr Lys Thr Asp Arg Cys Leu Gln Ala
                 165                 170

<210> SEQ ID NO 9
<211> LENGTH: 172
<212> TYPE: PRT
<213> ORGANISM: Rattus rattus
<220> FEATURE:
<223> OTHER INFORMATION: Rat OBP (UniProt ID P08937)

<400> SEQUENCE: 9

Met Val Lys Phe Leu Leu Ile Val Leu Ala Leu Gly Val Ser Cys Ala
1                 5                 10                 15

His His Glu Asn Leu Asp Ile Ser Pro Ser Glu Val Asn Gly Asp Trp
                 20                 25                 30

Arg Thr Leu Tyr Ile Val Ala Asp Asn Val Glu Lys Val Ala Glu Gly
                 35                 40                 45

Gly Ser Leu Arg Ala Tyr Phe Gln His Met Glu Cys Gly Asp Glu Cys
                 50                 55                 60

Gln Glu Leu Lys Ile Ile Phe Asn Val Lys Leu Asp Ser Glu Cys Gln
65                 70                 75                 80

Thr His Thr Val Val Gly Gln Lys His Glu Asp Gly Arg Tyr Thr Thr
                 85                 90                 95

Asp Tyr Ser Gly Arg Asn Tyr Phe His Val Leu Lys Lys Thr Asp Asp
                 100                 105                 110

Ile Ile Phe Phe His Asn Val Asn Val Asp Glu Ser Gly Arg Arg Gln
                 115                 120                 125

Cys Asp Leu Val Ala Gly Lys Arg Glu Asp Leu Asn Lys Ala Gln Lys
                 130                 135                 140

Gln Glu Leu Arg Lys Leu Ala Glu Glu Tyr Asn Ile Pro Asn Glu Asn
145                 150                 155                 160

Thr Gln His Leu Val Pro Thr Asp Thr Cys Asn Gln
                 165                 170

<210> SEQ ID NO 10
<211> LENGTH: 159
<212> TYPE: PRT
<213> ORGANISM: Bos gaurus
<220> FEATURE:
<223> OTHER INFORMATION: Bovine OBP (PDB ID 1OBP)

<400> SEQUENCE: 10

Ala Gln Glu Glu Glu Ala Glu Gln Asn Leu Ser Glu Leu Ser Gly Pro
1                 5                 10                 15

Trp Arg Thr Val Tyr Ile Gly Ser Thr Asn Pro Glu Lys Ile Gln Glu
                 20                 25                 30

Asn Gly Pro Phe Arg Thr Tyr Phe Arg Glu Leu Val Phe Asp Asp Glu
                 35                 40                 45

Lys Gly Thr Val Asp Phe Tyr Phe Ser Val Lys Arg Asp Gly Lys Trp
                 50                 55                 60

Lys Asn Val His Val Lys Ala Thr Lys Gln Asp Asp Gly Thr Tyr Val
65                 70                 75                 80

Ala Asp Tyr Glu Gly Gln Asn Val Phe Lys Ile Val Ser Leu Ser Arg
                 85                 90                 95
```

```
Thr His Leu Val Ala His Asn Ile Asn Val Asp Lys His Gly Gln Thr
        100                 105                 110

Thr Glu Leu Thr Gly Leu Phe Val Lys Leu Asn Val Glu Asp Glu Asp
        115                 120                 125

Leu Glu Lys Phe Trp Lys Leu Thr Glu Asp Lys Gly Ile Asp Lys Lys
        130                 135                 140

Asn Val Val Asn Phe Leu Glu Asn Glu Asp His Pro His Pro Glu
145                 150                 155
```

<210> SEQ ID NO 11
<211> LENGTH: 175
<212> TYPE: PRT
<213> ORGANISM: Sus scrofa
<220> FEATURE:
<223> OTHER INFORMATION: Boar OBP (PDB ID 1GM6)

<400> SEQUENCE: 11

```
His Lys Glu Ala Gly Gln Asp Val Val Thr Ser Asn Phe Asp Ala Ser
1                 5                   10                  15

Lys Ile Ala Gly Glu Trp Tyr Ser Ile Leu Leu Ala Ser Asp Ala Lys
        20                  25                  30

Glu Asn Ile Glu Glu Asn Gly Ser Met Arg Val Phe Val Glu His Ile
        35                  40                  45

Arg Val Leu Asp Asn Ser Ser Leu Ala Phe Lys Phe Gln Arg Lys Val
        50                  55                  60

Asn Gly Glu Cys Thr Asp Phe Tyr Ala Val Cys Asp Lys Val Gly Asp
65                  70                  75                  80

Gly Val Tyr Thr Val Ala Tyr Tyr Gly Glu Asn Lys Phe Arg Leu Leu
                85                  90                  95

Glu Val Asn Tyr Ser Asp Tyr Val Ile Leu His Leu Val Asp Val Asn
        100                 105                 110

Gly Asp Lys Thr Phe Gln Leu Met Glu Phe Tyr Gly Arg Lys Pro Asp
        115                 120                 125

Val Glu Pro Lys Leu Lys Asp Lys Phe Val Glu Ile Cys Gln Gln Tyr
        130                 135                 140

Gly Ile Ile Lys Glu Asn Ile Ile Asp Leu Thr Lys Ile Asp Arg Cys
145                 150                 155                 160

Phe Gln Leu Arg Gly Ser Gly Gly Val Gln Glu Ser Ser Ala Glu
                165                 170                 175
```

<210> SEQ ID NO 12
<211> LENGTH: 168
<212> TYPE: PRT
<213> ORGANISM: Ailuropoda melanoleuca
<220> FEATURE:
<223> OTHER INFORMATION: Panda OBP (PDB ID 5NGH)

<400> SEQUENCE: 12

```
His Glu Glu Gly Asn Asp Val Arg Arg Asn Phe Asp Val Ser Lys Ile
1                 5                   10                  15

Ser Gly Tyr Trp Tyr Ser Val Leu Leu Ala Ser Asp Val Arg Glu Lys
        20                  25                  30

Thr Glu Glu Asn Ser Ser Met Arg Val Phe Val Asn His Ile Glu Val
        35                  40                  45

Leu Ser Asn Ser Ser Leu Leu Phe Asn Met His Ile Lys Val Asp Gly
        50                  55                  60

Lys Cys Thr Glu Ile Ala Leu Val Ser Asp Lys Thr Glu Lys Asp Gly
65                  70                  75                  80
```

-continued

```
Glu Tyr Ser Val Glu Tyr Asp Gly Tyr Asn Val Phe Arg Ile Val Glu
                85                  90                  95

Thr Asp Tyr Thr Asp Tyr Ile Ile Phe His Leu Val Asn Phe Lys Glu
            100                 105                 110

Lys Asp Ser Phe Gln Met Met Glu Leu Ser Ala Arg Glu Pro Asp Thr
        115                 120                 125

Ser Glu Glu Val Arg Lys Arg Phe Val Glu Tyr Cys Gln Lys His Gly
    130                 135                 140

Ile Val Lys Glu Asn Ile Phe Asp Leu Thr Glu Val Asp Arg Cys Leu
145                 150                 155                 160

Gln Ala Arg Gly Ser Glu Lys Ala
                165
```

```
<210> SEQ ID NO 13
<211> LENGTH: 173
<212> TYPE: PRT
<213> ORGANISM: Cricetulus griseus
<220> FEATURE:
<223> OTHER INFORMATION: Chinese hamster OBP (Ensembl ID
      ENSCGRP00015014591.1)

<400> SEQUENCE: 13
```

```
Met Val Lys Phe Leu Leu Leu Ala Phe Ala Leu Ser Val Ser Cys Ala
1               5                   10                  15

His His Lys Ile Pro Glu Ile Ser Pro Ser Glu Val Asp Gly Lys Trp
            20                  25                  30

Arg Thr Leu Tyr Ile Gly Ala Asp Asn Thr Glu Lys Val Ile Gln Gly
        35                  40                  45

Gly Pro Leu Arg Ala Tyr Phe Arg His Met Glu Cys Ser Asp Glu Cys
    50                  55                  60

Gln Thr Leu Thr Ile Thr Phe Asn Thr Lys Glu Glu Gly Lys Cys Gln
65                  70                  75                  80

Thr His Thr Val Val Gly Arg Lys Asp Glu Asp Gly Gln Tyr Lys Thr
                85                  90                  95

Gly Phe Ser Gly Asn Asn Asp Phe His Val Val Glu Lys Ala Asp Gly
            100                 105                 110

Ile Ile Ile Phe His Asn Val Asn Val Asp Ser Ser Gly Lys Lys Thr
        115                 120                 125

Asn Val Ile Leu Val Ala Gly Lys Gly Lys Ser Leu Ser Lys Glu Gln
    130                 135                 140

Lys Glu Arg Leu Glu Asn Ile Ala Lys Glu Phe Asp Ile Ser Lys Glu
145                 150                 155                 160

Asn Ile Gln His Leu Val Pro Thr Asp Thr Cys Asp Gln
                165                 170
```

```
<210> SEQ ID NO 14
<211> LENGTH: 173
<212> TYPE: PRT
<213> ORGANISM: Sus scrofa domesticus
<220> FEATURE:
<223> OTHER INFORMATION: Meishan pig OBP (Ensembl ID
      ENSSSCP00040041163.1)

<400> SEQUENCE: 14
```

```
Met Lys Ser Leu Leu Leu Ser Leu Val Leu Gly Leu Val Cys Ala Gln
1               5                   10                  15

Glu Pro Gln Pro Glu Gln Asp Pro Phe Val Leu Ser Gly Lys Trp Ile
            20                  25                  30
```

```
Thr Ser Tyr Ile Gly Ser Ser Asp Leu Glu Lys Ile Gly Glu Asn Ala
        35              40              45

Pro Phe Gln Val Phe Met Arg Ser Ile Glu Phe Asp Asp Lys Glu Ser
    50              55              60

Lys Val Tyr Leu Asn Phe Phe Ser Lys Glu Asn Gly Ile Cys Glu Glu
65              70              75              80

Phe Ser Leu Ile Gly Thr Lys Gln Glu Gly Asn Thr Tyr Asp Val Asn
                85              90              95

Tyr Ala Gly Asn Asn Lys Phe Val Val Ser Tyr Ala Ser Glu Thr Ala
            100             105             110

Leu Ile Ile Ser Asn Ile Asn Val Asp Glu Glu Gly Asp Lys Thr Ile
            115             120             125

Met Thr Gly Leu Leu Gly Lys Gly Thr Asp Ile Glu Asp Gln Asp Leu
    130             135             140

Glu Lys Phe Lys Glu Val Thr Arg Glu Asn Gly Ile Pro Glu Glu Asn
145             150             155             160

Ile Val Asn Ile Ile Glu Arg Asp Asp Cys Pro Ala Lys
                165             170
```

<210> SEQ ID NO 15
<211> LENGTH: 175
<212> TYPE: PRT
<213> ORGANISM: Equus caballus
<220> FEATURE:
<223> OTHER INFORMATION: Horse OBP (Ensembl ID ENSECAP00000000103.2)

<400> SEQUENCE: 15

```
Met Gln Ile Leu Leu Leu Ser Leu Val Leu Gly Val Val Cys Ala Val
1               5               10              15

Gln Glu Pro Gln Ser Glu Thr Asp Tyr Ser Leu Phe Ser Gly Glu Trp
            20              25              30

Asn Thr Ile Tyr Ile Gly Ser Ser Asn Ile Glu Lys Ile Ser Glu Asn
        35              40              45

Gly Pro Phe Arg Ile Leu Leu Arg Arg Leu Asp Leu Asp Ser Ala Gly
    50              55              60

Asp Arg Ile Ile Tyr Thr Phe Phe Leu Lys Val Asn Gly Gln Cys Thr
65              70              75              80

Lys Ile Ser Ser Leu Ala Ile Lys Thr Glu Glu Asn Thr Tyr Val Cys
                85              90              95

His Tyr Ala Gly Lys Asn Lys Phe Glu Ile Leu His Leu Ser Lys Thr
            100             105             110

Ala Ile Ile Ile Asp Ile Val Asn Glu Asp Glu Gly Gly Leu Val Thr
            115             120             125

Lys Met Val Ala Leu Val Gly Met Leu Gly Asp Ile Gln Lys Glu Asp
    130             135             140

Ile Glu Lys Phe Lys Glu Val Ala Lys Glu Lys Glu Ile Pro Glu Glu
145             150             155             160

Asn Ile Val Asn Ile Ile Asn Ile Asp Asp Cys Pro Thr Ser Glu
                165             170             175
```

<210> SEQ ID NO 16
<211> LENGTH: 170
<212> TYPE: PRT
<213> ORGANISM: Cavia porcellus
<220> FEATURE:
<223> OTHER INFORMATION: Guinea pig OBP ((Ensembl ID
        ENSCPOP00000016393.2)

-continued

<400> SEQUENCE: 16

```
Met Gln Ile Leu Leu Leu Ala Leu Thr Ile Gly Leu Ala Tyr Ala His
1               5                   10                  15

Gln Thr Leu Asp Pro Ser Glu Ile Asn Gly Gln Trp His Thr Ile Ser
            20                  25                  30

Ile Ala Ala Asp Asn Val Glu Lys Ile Gly Glu Gly Gly Pro Leu Arg
        35                  40                  45

Gly Tyr Phe His Asn Leu His Cys Tyr Asp Gly Cys Lys Asn Ile Gly
    50                  55                  60

Leu Thr Phe Tyr Val Lys Leu Asp Gly Asn Cys Gln Arg Phe Asp Val
65                  70                  75                  80

Leu Gly Ala Lys Gln Glu Asp Ser Asp Val Tyr Val Ala Gln Tyr Ser
                85                  90                  95

Gly Thr Asn His Phe Glu Val Ile Gly Lys Lys Glu Asp Ala Ile Ala
            100                 105                 110

Phe Tyr Asn His Asn Thr Asp Glu Thr Gly Lys Glu Thr Lys Met Ile
            115                 120                 125

Val Val Val Ala Arg Arg Asp Ser Leu Thr Glu Glu Glu Gln Gln Lys
    130                 135                 140

Leu Gln Glu Val Ala Gly Glu Lys Gly Ile Pro Lys Asp Asn Ile Arg
145                 150                 155                 160

Tyr Phe Arg Glu Arg Asp Thr Cys Ala Gln
                165                 170
```

<210> SEQ ID NO 17
<211> LENGTH: 174
<212> TYPE: PRT
<213> ORGANISM: Canis lupus
<220> FEATURE:
<223> OTHER INFORMATION: Dog OBP ((Ensembl ID ENSCAFP00040020992.1)

<400> SEQUENCE: 17

```
Met Lys Ile Leu Leu Leu Cys Leu Ile Leu Val Leu Ala Cys Asp Ala
1               5                   10                  15

His Leu Pro Leu Pro Asn Val Leu Thr Gln Val Ser Gly Pro Trp Lys
            20                  25                  30

Thr Leu Tyr Val Ser Ser Asn Asn Leu Asp Lys Ile Ala Glu Asn Gly
        35                  40                  45

Pro Phe Arg Ile Tyr Ile Arg Arg Ile Asn Val Asp Ile Pro Arg Leu
    50                  55                  60

Lys Ile Leu Phe Ser Phe Phe Val Lys Val Asp Gly Glu Cys Val Glu
65                  70                  75                  80

Lys Ser Val Glu Ala Ser Ile Gly Gln Asp Asn Leu Ile Asn Ala His
                85                  90                  95

Tyr Ala Gly Gly Asn Tyr His Gln Ile Leu Asp Val Thr Pro Asn Ala
            100                 105                 110

Leu Ile Gly Tyr Ile Val Asn Val Asp Asp Lys Gly Arg Ile Thr Lys
            115                 120                 125

Leu Ala Ser Leu Val Gly Arg Gly Ala His Val Asn Glu Glu Asp Ile
    130                 135                 140

Ala Lys Phe Lys Lys Leu Ser Arg Glu Lys Gly Ile Pro Glu Glu Asn
145                 150                 155                 160

Ile Ile Tyr Leu Gly Asp Thr Asp Asn Cys Pro Asn His Glu
                165                 170
```

```
<210> SEQ ID NO 18
<211> LENGTH: 173
<212> TYPE: PRT
<213> ORGANISM: Sus scrofa domesticus
<220> FEATURE:
<223> OTHER INFORMATION: Tibetan pig OBP (Ensembl ID
      ENSSSCP00015013912.1)

<400> SEQUENCE: 18

Met Lys Ser Leu Leu Leu Ser Leu Val Leu Gly Leu Val Cys Ala Gln
1               5                   10                  15

Glu Pro Gln Pro Glu Gln Asp Pro Phe Glu Leu Ser Gly Lys Trp Ile
            20                  25                  30

Thr Ser Tyr Ile Gly Ser Ser Asp Leu Glu Lys Ile Gly Glu Asn Ala
        35                  40                  45

Pro Phe Gln Val Phe Met Arg Ser Ile Glu Phe Asp Asp Lys Glu Ser
    50                  55                  60

Lys Val Tyr Leu Asn Phe Phe Ser Lys Glu Asn Gly Ile Cys Glu Glu
65                  70                  75                  80

Phe Ser Leu Thr Gly Thr Lys Gln Glu Gly Asn Thr Tyr Asp Val Asn
                85                  90                  95

Tyr Ala Gly Asn Asn Lys Phe Val Val Ser Tyr Ala Ser Glu Thr Ala
            100                 105                 110

Leu Ile Ile Ala Asn Ile Asn Val Asp Glu Glu Gly Asp Lys Thr Ile
            115                 120                 125

Met Thr Gly Leu Leu Gly Lys Gly Thr Asp Ile Glu Asp Gln Asp Leu
    130                 135                 140

Glu Lys Phe Lys Glu Val Thr Arg Glu Asn Gly Ile Pro Glu Glu Asn
145                 150                 155                 160

Ile Val Asn Ile Ile Glu Arg Asp Asp Cys Pro Ala Lys
                165                 170

<210> SEQ ID NO 19
<211> LENGTH: 314
<212> TYPE: PRT
<213> ORGANISM: Sus scrofa domesticus
<220> FEATURE:
<223> OTHER INFORMATION: Cat felis OBP (Ensembl ID ENSFCAP00000053707.1)

<400> SEQUENCE: 19

Arg Ser Cys Val Ile His Leu Gln Cys Leu Pro Thr Gly Cys Leu Phe
1               5                   10                  15

Ser Ala Leu His Asn Gly Leu Pro Asp Gly Arg Leu Pro Leu Pro Asp
            20                  25                  30

Gly Arg Leu Pro Leu Pro Asp Gly Arg Leu Pro Leu Pro Asp Ser Arg
        35                  40                  45

Leu Pro Leu Pro Asp Gly Arg Leu Pro Leu Pro Asp Gly Arg Leu Pro
    50                  55                  60

Leu Pro Asp Gly Arg Leu Pro Leu Pro Asp Gly Arg Leu Pro Leu Pro
65                  70                  75                  80

Asp Gly Arg Leu Pro Leu Pro Asp Gly Arg Leu Pro Leu Pro Asp Gly
                85                  90                  95

Arg Leu Pro Leu Pro Asp Gly Arg Leu Pro Leu Pro Glu Gly Arg Leu
            100                 105                 110

Pro Leu Pro Asp Ser His Pro Pro Leu Gln Asp Asn Leu Thr Gln Leu
            115                 120                 125

Ser Gly Glu Trp Asn Thr Leu Leu Val Ala Ala Thr Asn Val Asp Lys
```

-continued

```
         130                 135                 140

Ile Ser Asn Gly Pro Phe His Gly Tyr Ile Cys Lys Val Asp Val Asp
145                 150                 155                 160

Val Thr Asn Gly Thr Val Val Phe Asn Phe Ser Val Met Met Asn Gly
                    165                 170                 175

Arg Cys Thr Glu Lys Ser Ala Val Gly Thr Ile Gly Arg Asp Lys Phe
                180                 185                 190

Ile Asn Ile Gly Ser Met Asn Gln Asn Leu Phe Asn Leu Phe Ser Val
                195                 200                 205

Thr Ser Asn Thr Ile Ala Ile Asn Val Asn Thr Arg Arg Asn Thr Thr
        210                 215                 220

Lys Ala Phe Ala Leu Leu Asp Thr Asn Gly Asn Ile Phe Asn Ile Gly
225                 230                 235                 240

Tyr Asp Ser Leu Gly Ser Leu Ile Ile His Thr Ala Asn Val Asp Thr
                245                 250                 255

Ala Gly Gln Thr Thr Gln Val Phe Ala Leu Leu Gly Lys Arg Leu His
                260                 265                 270

Pro Asp Asp Asn Asp Phe Ala Lys Phe Arg Glu Leu Met Arg Glu Asn
                275                 280                 285

Asn Ile Pro Glu Glu Asn Leu Ile Asp Met Ser Lys Thr Glu Lys Cys
        290                 295                 300

Pro Lys Lys Glu Lys Gly Thr Asn Pro Ser
305                 310

<210> SEQ ID NO 20
<211> LENGTH: 175
<212> TYPE: PRT
<213> ORGANISM: Pan troglodytes
<220> FEATURE:
<223> OTHER INFORMATION: Chimpanzee OBP (Ensembl ID
      ENSPTRP00000048681.3)

<400> SEQUENCE: 20

Met Ala Leu Leu Leu Leu Ser Leu Gly Leu Ser Leu Ile Thr Ala Gln
1               5                   10                  15

Glu Phe Asp Pro Arg Asn Val Met Gln Arg Asn Tyr Asn Met Ala Arg
                20                  25                  30

Val Ser Gly Val Trp Tyr Ser Ile Phe Met Ala Asp Asp Leu Asn Arg
            35                  40                  45

Ile Lys Glu Asn Gly Asp Leu Arg Val Phe Val Gln Asn Ile Glu His
        50                  55                  60

Leu Lys Asn Gly Ser Leu Lys Phe Asp Phe Glu Tyr Met Val Gln Gly
65                  70                  75                  80

Glu Cys Val Ala Val Val Val Cys Glu Lys Thr Glu Lys Asn Gly
                85                  90                  95

Glu Tyr Ser Ile Asn Tyr Glu Gly Gln Asn Thr Val Ala Val Ser Glu
                100                 105                 110

Thr Asp Tyr Arg Leu Phe Ile Thr Phe His Leu Gln Asn Phe Arg Asn
                115                 120                 125

Gly Thr Glu Thr His Thr Leu Ala Leu Tyr Glu Thr Cys Lys Lys Tyr
        130                 135                 140

Gly Leu Gly Ser Gln Asn Ile Ile Asn Leu Thr Asn Lys Asp Pro Cys
145                 150                 155                 160

Tyr Ser Lys His Tyr Arg Ser Pro Pro Arg Pro Pro Met Arg Glu
                165                 170                 175
```

-continued

```
<210> SEQ ID NO 21
<211> LENGTH: 210
<212> TYPE: PRT
<213> ORGANISM: Artificial Sequence
<220> FEATURE:
<223> OTHER INFORMATION: OBP::GQ20::KP (recombinant protein)

<400> SEQUENCE: 21

Gln Glu Pro Gln Pro Glu Gln Asp Pro Phe Glu Leu Ser Gly Lys Trp
1               5                   10                  15

Ile Thr Ser Tyr Ile Gly Ser Ser Asp Leu Glu Lys Ile Gly Glu Asn
            20                  25                  30

Ala Pro Phe Gln Val Phe Met Arg Ser Ile Glu Phe Asp Asp Lys Glu
        35                  40                  45

Ser Lys Val Tyr Leu Asn Phe Phe Ser Lys Glu Asn Gly Ile Cys Glu
    50                  55                  60

Glu Phe Ser Leu Ile Gly Thr Lys Gln Glu Gly Asn Thr Tyr Asp Val
65                  70                  75                  80

Asn Tyr Ala Gly Asn Asn Lys Phe Val Val Ser Tyr Ala Ser Glu Thr
                85                  90                  95

Ala Leu Ile Ile Ser Asn Ile Asn Val Asp Glu Glu Gly Asp Lys Thr
            100                 105                 110

Ile Met Thr Gly Leu Leu Gly Lys Gly Thr Asp Ile Glu Asp Gln Asp
            115                 120                 125

Leu Glu Lys Phe Lys Glu Val Thr Arg Glu Asn Gly Ile Pro Glu Glu
        130                 135                 140

Asn Ile Val Asn Ile Ile Glu Arg Asp Asp Cys Pro Ala Gly Gln Gly
145                 150                 155                 160

Gln Gly Gln Gly Gln Gly Gln Gly Gln Gly Gln Gly Gln Gly Gln Gly
                165                 170                 175

Gln Gly Gln Gly Gln Gly Gln Gly Gln Gly Gln Gly Gln Gly Gln Gly
            180                 185                 190

Gln Gly Gln Gly Gln Gly Gly Val Cys Gly Pro Ser Pro Cys Ile
            195                 200                 205

Thr Thr
    210

<210> SEQ ID NO 22
<211> LENGTH: 349
<212> TYPE: PRT
<213> ORGANISM: Artificial Sequence
<220> FEATURE:
<223> OTHER INFORMATION: OBP::GQ20::CBM (recombinant protein)

<400> SEQUENCE: 22

Gln Glu Pro Gln Pro Glu Gln Asp Pro Phe Glu Leu Ser Gly Lys Trp
1               5                   10                  15

Ile Thr Ser Tyr Ile Gly Ser Ser Asp Leu Glu Lys Ile Gly Glu Asn
            20                  25                  30

Ala Pro Phe Gln Val Phe Met Arg Ser Ile Glu Phe Asp Asp Lys Glu
        35                  40                  45

Ser Lys Val Tyr Leu Asn Phe Phe Ser Lys Glu Asn Gly Ile Cys Glu
    50                  55                  60

Glu Phe Ser Leu Ile Gly Thr Lys Gln Glu Gly Asn Thr Tyr Asp Val
65                  70                  75                  80

Asn Tyr Ala Gly Asn Asn Lys Phe Val Val Ser Tyr Ala Ser Glu Thr
                85                  90                  95
```

-continued

```
Ala Leu Ile Ile Ser Asn Ile Asn Val Asp Glu Glu Gly Asp Lys Thr
            100                 105                 110

Ile Met Thr Gly Leu Leu Gly Lys Gly Thr Asp Ile Glu Asp Gln Asp
            115                 120                 125

Leu Glu Lys Phe Lys Glu Val Thr Arg Glu Asn Gly Ile Pro Glu Glu
    130                 135                 140

Asn Ile Val Asn Ile Ile Glu Arg Asp Asp Cys Pro Ala Gly Gln Gly
145                 150                 155                 160

Gln Gly Gln Gly Gln Gly Gln Gly Gln Gly Gln Gly Gln Gly Gln Gly
                165                 170                 175

Gln Gly Gln Gly Gln Gly Gln Gly Gln Gly Gln Gly Gln Gly Gln Gly
                180                 185                 190

Gln Gly Gln Gly Gln Ala Ser Pro Ile Gly Glu Gly Thr Phe Asp Asp
            195                 200                 205

Gly Pro Glu Gly Trp Val Ala Tyr Gly Thr Asp Gly Pro Leu Asp Thr
    210                 215                 220

Ser Thr Gly Ala Leu Cys Val Ala Val Pro Ala Gly Ser Ala Gln Tyr
225                 230                 235                 240

Gly Val Gly Val Val Leu Asn Gly Val Ala Ile Glu Glu Gly Thr Thr
                245                 250                 255

Tyr Thr Leu Arg Tyr Thr Ala Thr Ala Ser Thr Asp Val Thr Val Arg
            260                 265                 270

Ala Leu Val Gly Gln Asn Gly Ala Pro Tyr Gly Thr Val Leu Asp Thr
            275                 280                 285

Ser Pro Ala Leu Thr Ser Glu Pro Arg Gln Val Thr Glu Thr Phe Thr
    290                 295                 300

Ala Ser Ala Thr Tyr Pro Ala Thr Pro Ala Ala Asp Asp Pro Glu Gly
305                 310                 315                 320

Gln Ile Ala Phe Gln Leu Gly Gly Phe Ser Ala Asp Ala Trp Thr Leu
            325                 330                 335

Cys Leu Asp Asp Val Ala Leu Asp Ser Glu Val Glu Leu
            340                 345
```

FRAGRANCE RELEASE MECHANISM, METHOD AND USES THEREOF

CROSS REFERENCE

This application is a § 371 U.S. National Stage Entry of International Application No. PCT/IB2021/056011, filed Jul. 5, 2021, which claims the benefit of Portuguese Application No. 1165611, filed Jul. 3, 2020, and European Application No. 202006292.3, filed Nov. 6, 2020, each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Dec. 16, 2022, is named 63230-716-831_Sequence_Listing.txt and is 36,836 bytes in size.

TECHNICAL FIELD

The present disclosure relates to a mechanism of adsorption and dissociation involving fragrance molecule and an odorant-binding protein (OBP-I) regulated simultaneously by human sweat and temperature. This system can be used in cosmetic formulations where the fragrances are released upon presence of sweat at body temperature.

BACKGROUND

Odorant-binding proteins (OBPs) are small water-soluble proteins, belonging to lipocalins superfamily.[1-2] They are responsible to transport hydrophobic odorous molecules, called odorants, in their calyx-shaped cavity, across the aqueous mucus barrier towards the olfactory receptors, where a cascade of transduction signal is traduced in the brain's interpretation.[3-4] These proteins are also described as involved in removing odorants from the olfactory receptors after their stimulation.[5-6]

Several mammalian odorant-binding proteins have been identified and some of them isolated from nasal mucus such as bovine, pig, boar, panda, mice, rats and humans.[7-13]

DNA sequences of mammalian OBPs present low similarity: porcine OBP (OBP-I) and human OBP (hOBP$_{IIa}$) present only 13.9% of DNA sequence similarity; OBP-I and bovine OBP present 42.7%.[4] Despite wide genetic variability between OBPs from different mammalian species, lipocalin members present few characteristic signatures that allow their identification as the case of the conserved tertiary structure, presenting a β-barrel structure composed by eight β-strands linked by seven loops and connected to a short α-helix close to the C-terminus and a ninth β-strand followed by the disordered C-terminal tail.[14-16] The structure of OBPs is highly stable and resistant to degradation by temperature, organic solvents, pH variation, or proteolytic digestion.[17-18] [19] The FT-IR spectra for porcine OBP revealed a structure exceptionally stable to thermal denaturation (up to 80° C.), particularly in the presence of a ligand.[20] Furthermore, vertebrate OBPs show capacity to reverse the unfolding of protein even after denaturation.[20]

Human body produces unpleasant odours associated with stress, anxiousness, nervousness and physical exercise.[21] To prevent or reduce their occurrence, antibacterial agents and fragrances are commonly added to cosmetic formulations. However, drawbacks related with the limited effect against different odours and with the residual amount of these deodorants are detected in clothing and skin.[22]

OBPs have affinity for several molecules associated with odorific feeling. All those molecules are volatile and detected by OBPs at very low concentrations, being a system highly sensitive. The fast responsive time of the OBPs and the high stability of these proteins create an excellent biological element as biosensor for detection of the dangerous substances and pathogens, pesticides and drugs present in food or water[18, 23] as well as the potential use as deodorizer and medical diagnostics.[24-25]

Odorific molecules can be associated with pleasant or unpleasant feelings. OBP have affinities for all molecules associated with odors.[3-4] Fragrances are compositions containing odorific molecules with pleasant feeling.

The use of 1-aminoanthracene (1-AMA) as odour model molecule provides a capacity to measure the binding capacity of odorant-binding protein, by fluorescence assay. The free 1-AMA and 1-AMA bound to pig OBP-I can be quantified measuring the fluorescence with excitation wavelength at 295 nm. The maximum wavelength of 1-AMA bound to OBP-I is shifted from 537 nm to 481 nm.[20] The non-fluorescence odorant can be measured by competitive assays or by gas chromatography-mass spectrometry.

The following works already reported the interaction between OBPs and odour model molecules, as well as with lipidic structures such as liposomes.

Filipa Gonçalves et at (2018) "Two Engineered OBPs with opposite temperature-dependent affinities towards 1-aminoanthracene" mentions two recombinant proteins based on pig OBP sequence (i) truncated OBP (tOBP-F44A/F66A) obtained from the deletion of the first 16 residues of the N-terminal and the replacement of two phenylalanine residues at the binding pocket by alanine residues (F44A and F66A), and (ii) OBP::GQ$_{20}$::SP-DS3 resulted of the fusion of OBP-I with a spacer of 20 repetitions of glycine-glutamine residues and the anchor peptide SP-DS3.[34] Experimental and molecular modelling data showed that 1-AMA model ligand binds preferentially to tOBP-F44A/F66A at 25° C. while ligand binds to OBP::GQ$_{20}$::SP-DS3 favourably at 37° C.[34]

Filipa Gonçalves et al (2018) "OBP fused with cell-penetrating peptides promotes liposomal transduction" report the fusion of porcine OBP with cell-penetrating peptides (CPPs, e.g. TAT, Pep-1 and pVEC). The study revealed different efficiencies on 1-AMA transduction into liposomes.[30]

Filipa Gonçalves et al (2018) "1-Aminoanthracene Transduction into Liposomes Driven by Odorant-Binding Protein Proximity" discloses the design of two fusion proteins based on pig OBP fused with anchor peptide SP-DS3[32] in absence and presence of a spacer (GQ$_{20}$). This work demonstrated that the 1-AMA transduction into liposomes is driven by proximity of protein anchored to liposomal membrane (advantage for absence of spacer).[33]

Filipa Gonçalves et al (2019) "Release of Fragrances from Cotton Functionalized with Carbohydrate-Binding Module Proteins" discloses the design of fusion protein based on pig OBP fused with a spacer (GQ$_{20}$) and a carbohydrate binding module (CBM). The work demonstrated the affinity of protein to one fragrance (β-citronellol) and the release of this fragrance from cotton in presence of sweat.[25] Regardless, the release capacity in the presence of sweat is inferior as compared to the native OBP.

Alessandro Capo et at (2018) "The porcine odorant-binding protein as molecular probe for benzene detection"

discloses pig odorant-binding protein to be used as probe for benzene detection in atmosphere, through fluorescence assay.[28]

Nunzio Cennamo et at (2015) "Easy to Use Plastic Optical Fiber-Based Biosensor for Detection of Butanal" reports the detection of butanal (20-1000 μM) by porcine odorant-binding protein through competitive assay. This aldehyde is very toxic, exhibiting high risks for human health like cytotoxicity and cancer. The authors describe an optical biosensor to detect butanol in liquid samples.[27]

Carla Silva et at (2014) "Odorant binding proteins: a biotechnological tool for odour control" discloses the application of porcine odorant-binding protein for release of fragrances from a cotton fabric to mask smoke odour. The authors confirmed the functionalization of OBP on fabrics. They tested only the release of one fragrance from textile. Contrary to the work of Silva et al., the present disclosure includes the release mechanism of different fragrances or other molecules as response of human perspiration with upper efficiency. Additionally, the subject-matter of the present disclosure is suitable for use in textile and cosmetic fields.

Paolo Pelosi et at (2014) "Structure and biotechnological applications of odorant-binding proteins" discloses the possibility of OBPs to be used as a sensor to detect volatile and slow release of odorant molecules.

Lei Han et al (2014) "Operating Mechanism and Molecular Dynamics of Pheromone-Binding Protein ASP1 as Influenced by pH" indicates pheromone-binding protein ASP1 as binds odorants at low pH and the dissociation respond to pH change. The authors describe the benefit of this research in biotechnology and agriculture. The results were determined by molecular docking and dynamics simulations.

Alberto Mazzini et at (2007) "Dissociation and unfolding of bovine odorant binding protein at acidic pH" discloses the structure of bovine OBP at neutral and acidic pH, by molecular simulation.

Mariella Parisi et at (2003) "Unfolding and refolding of porcine odorant binding protein in guanidinium hydrochloride: equilibrium studies at neutral pH" discloses the denaturant effect of guanidinium hydrochloride, a well-known chaotropic agent, in folding/unfolding of protein. The aim of this fundamental study was to understand the structure of the OBP protein, in particular its unfolding and refolding process.

Document WO 0123890A1 discloses a detector array based on sensing elements within a solid support with use for clinical samples or cell extracts, in gaseous state. It is an immunoassay utilizing viral peptides.

Document EP0335654A3 discloses the method for gene isolation of odorant-binding protein from rat and a protein production method.

Document WO2001012806A3 described OBPII as a fixer of hydrophobic ligands such as odours that can be used for personal hygiene, agri-food system and nutritional and therapeutic uses.

These facts are disclosed in order to illustrate the technical problem addressed by the present disclosure.

GENERAL DESCRIPTION

The present disclosure is related to adsorption and dissociation mechanism of native odorant-binding protein (OBP-I), in particular pig OBP-I (SEQ. ID NO. 1), and OBP fused with linker GQ 20× and KP peptide (OBP::GQ$_{20}$::KP, SEQ. ID NO. 21). These proteins have a negative charge of approximately −20 (pH 7.4) due to the high content in aspartic acid and glutamic acid residues. The isoelectric point value of these proteins are between 4.08 and 4.65.[26]

In an embodiment, the solution here disclosed can have a high impact in human social life that are associated with perspiration issues. The system has several advantages including the use of bioinspired cosmetic bioingredients (green solutions) without damaging for the ecosystems.

The mechanism here disclosed divulge that odorant-binding protein, in particular porcine odorant-binding protein (OBP-I), presents high affinity (adsorption) to fragrances in 50 mM Tris-HCl pH 7.5 buffer, at 37° C. The affinity constant (Ka) of OBP-I was of $4.00\pm0.03$ μM. On the other hand, OBP-I presents a reverse mechanism, i.e., the dissociation of fragrance from its binding pocket with reduced Ka ($0.20\pm0.02$ μM) when in exposition of perspiration (sweat), even at different pH (range of 4.0-8.5, Table 2). Similarity, OBP::GQ$_{20}$::KP presents high affinity to fragrances in buffer, at 37° C. (Ka=$4.00\pm0.04$ μM) that is reduced in presence of an electrolyte solution, such as sweat (Ka=$0.59\pm0.01$ μM). Therefore, OBPs presents reduced affinity when in contact with perspiration, releasing the fragrance in this condition.

Surprisingly, OBP::GQ$_{20}$::KP (SEQ ID NO. 21) showed 6.8× more fragrance release in presence of sweat versus the presence of buffer. These values are superior to the values reported in state of art, in particular to the values reported for OBP::GQ$_{20}$::CBM (SEQ ID NO. 22), where the release mechanism showed 1.3× release of fragrance in presence of sweat.[25]

The adsorption and dissociation mechanism of porcine odorant-binding protein can be done in a repeated manner.

Human sweat can be used as a trigger to release/dissociate a fragrance from OBP-I. Therefore, the subject-matter of the present disclosure can be used in skin care products as well as in textile items, in particular clothes.

In an embodiment, the present disclosure relates to a protein with an amino acid sequence similar to mammalians odorant-binding proteins to be incorporated in formulations for cosmetic or textile applications.

In an embodiment, the native form of odorant-binding protein may be from pig, human, dog, cat, rat, mouse, cow, boar, panda, Chinese hamster, Meishan pig, Guinea pig, Tibetan pig, horse, dolphin and chimpanzee.

In an aspect of the present disclosure, applications of the present subject-matter may be based on the release of odorant molecules from odorant-binding protein, triggered by electrolyte solutions at body temperature.

In an embodiment, the electrolyte solution refers to a solution with a NaCl concentration higher than 9.5 grams/L, in particular to a solution with a NaCl concentration ranging from 9.5 to 45 grams/L. Preferably, the electrolyte solution is human sweat, pet sweat, salty water or micellar water.

In an embodiment, human sweat may comprise water, lactic acid, urea and minerals, such as sodium, potassium, calcium, and magnesium.

In an embodiment, cosmetic applications may be for skin and hair care. Skin care applications may be related with OBPs formulated in specialty formulations for skin creams, lipsticks, lips creams and face mask powders, face and body creams, skin clarifiers, primers and foundations.

In a further embodiment, hair care applications may be related with OBPs formulated in eyelash mascaras, hair shampoos, hair serum, hairs masks, hair conditioners, or hair coloration creams.

The present disclosure relates to a release composition comprising an isolated or artificial protein with at least 90% of identity with an amino acid sequence selected from the following list: SEQ. ID NO. 1, SEQ. ID NO. 2, SEQ. ID NO. 3, SEQ. ID NO. 4, SEQ. ID NO. 5, SEQ. ID NO. 6, SEQ. ID NO. 7, SEQ. ID NO. 8, SEQ. ID NO. 9, SEQ. ID NO. 10, SEQ. ID NO. 11, SEQ. ID NO. 12, SEQ. ID NO. 13, SEQ. ID NO. 14, SEQ. ID NO. 15. SEQ. ID NO. 16, SEQ. ID NO. 17, SEQ. ID NO. 18, SEQ. ID NO. 19, SEQ. ID NO. 20, SEQ. ID NO. 21, or mixtures thereof, preferably 91% identical, 92% identical, 93% identical, 94% identical, 95% identical, 96% identical, 97% identical, 98% identical, 99% identical or identical; an active agent selected from a list comprising a deodorizing agent, a natural essence, a fragrance, a moisturizing agent, or mixtures thereof; wherein the active agent is bounded to the protein; and wherein the protein releases the active agent in the presence of an electrolyte solution, at a temperature between 10-60° C.

In an embodiment, the release composition comprises an isolated or artificial unmodified protein with at least 90% of identity with an amino acid sequence selected from the following list: SEQ. ID NO. 1, SEQ. ID NO. 2, SEQ. ID NO. 3, SEQ. ID NO. 4, SEQ. ID NO. 5, SEQ. ID NO. 6, SEQ. ID NO. 7, SEQ. ID NO. 8, SEQ. ID NO. 9, SEQ. ID NO. 10, SEQ. ID NO. 11, SEQ. ID NO. 12, SEQ. ID NO. 13, SEQ. ID NO. 14, SEQ. ID NO. 15. SEQ. ID NO. 16, SEQ. ID NO. 17, SEQ. ID NO. 18, SEQ. ID NO. 19, SEQ. ID NO. 20, SEQ. ID NO. 21, or mixtures thereof, preferably 91% identical, 92% identical, 93% identical, 94% identical, 95% identical, 96% identical, 97% identical, 98% identical, 99% identical or identical.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (over the whole the sequence) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. The sequence identity values, which are indicated in the present subject matter as a percentage were determined over the entire amino acid sequence, using BLAST with the default parameters.

In an embodiment, the composition of the present subject-matter comprises 0.01 to 5000 μM of the unmodified protein.

In an embodiment, the composition of the present subject-matter comprises 0.01 to 5000 μM of the protein.

In another embodiment, the release composition comprises 0.1 μM to 2 M of active agent, preferably 0.2 μM to 1 M.

In an embodiment, the protein has an affinity constant of 1-4.5 μM to the active agent, in water or buffer solutions, preferably Tris-HCl, phosphate solution, and/or phosphate buffered saline. In a further embodiment, the affinity constant of the protein to the active agent ranges between 0.1-0.99 μM in the electrolyte solution, preferably in sweat.

The present disclosure relates to a fragrance release composition comprising: 0.01 to 5000 μM of an isolated or artificial protein with at least 90% of identity with an amino acid sequence selected from the following list: SEQ. ID NO. 1, SEQ. ID NO. 2, SEQ. ID NO. 3, SEQ. ID NO. 4, SEQ. ID NO. 5, SEQ. ID NO. 6, SEQ. ID NO. 7, SEQ. ID NO. 8, SEQ. ID NO. 9, SEQ. ID NO. 10, SEQ. ID NO. 11, SEQ. ID NO. 12, SEQ. ID NO. 13, SEQ. ID NO. 14, SEQ. ID NO. 15. SEQ. ID NO. 16, SEQ. ID NO. 17, SEQ. ID NO. 18, SEQ. ID NO. 19, SEQ. ID NO. 20, SEQ. ID NO. 21 or mixtures thereof; 0.1 μM to 2 M of an active agent selected from a list comprising a deodorizing agent, a natural essence, a fragrance, a moisturizing agent, or mixtures thereof; wherein the active agent is bounded and/or entrapped to the protein; and wherein the protein releases the active agent in the presence of an electrolyte solution, at a temperature between 10-70° C., preferably 10-60° C.; wherein the affinity constant of the protein to the active agent, in water, ranges between 1-4.5 μM; wherein the active agent has a molecular weight from 20 to 1000 g/mol; wherein the electrolyte solution is sweat, salty water or micellar water.

In an embodiment, the active agent has a molecular weight between 20 to 1000 g/mol, preferably 75-300 g/mol. In a further embodiment, the active agent is a fragrance molecule. In a yet further embodiment, the bioactive agent comprises a functional group selected from aromatic, aldehyde or alcohols. In a yet further embodiment, the active agent is a fragrance molecule, selected from a list comprising the molecules listed in Table 1.

TABLE 1

| List of fragrances and their properties. | | | | |
|---|---|---|---|---|
| CAS# | Name | Odor description | Chemical Family | MW (g/mol) |
| 85213-22-5 | 2-acetyl-1-pyrroline | roasted/bread | ketone | 111.14 |
| 8000-41-7 | α-terpineol | lilac | alcohol/terpene | 154.25 |
| 502-99-8 | β-ocimene | sweet herbal | hydrocarbon/terpene | 136.24 |
| 140-11-4 | benzyl acetate | strawberry/pear | ester | 150.17 |
| 123-86-4 | butyl acetate | banana | ester | 116.16 |
| 76-22-2 | camphor | camphora | ketone/terpene | 152.24 |
| 6485-40-1 | carvone | mint | ketone/terpene | 150.22 |
| 5392-40-5 | citral | lemon/citrus | aldehyde/terpene | 152.24 |
| 106-22-9 | citronellol | citronella/rose-like | alcohol/terpene | 156.27 |
| 91-64-5 | coumarin | sweet vanilla/pleasant | lactone/aromatic | 146.15 |
| 431-03-8 | diacetyl | buttery | ketone | 86.09 |
| 97-53-0 | eugenol | cloves | aromatic alcohol | 164.20 |
| 6413-10-1 | fructone | apple | ester | 174.19 |
| 706-14-9 | gamma decalactone | coconut | lactone | 170.25 |

TABLE 1-continued

| List of fragrances and their properties. | | | | |
|---|---|---|---|---|
| CAS# | Name | Odor description | Chemical Family | MW (g/mol) |
| 104-61-0 | gamma nonalactone | peach/fruity | lactone | 156.23 |
| 106-24-1 | geraniol | floral/sweet rose | terpene | 154.24 |
| 24851-98-7 | hedione | floral/jasmine | ester | 226.32 |
| 123-92-2 | isoamyl acetate | pear/banana | ester | 130.19 |
| 67920-63-2 | lilac aldehyde | floral/lilac | aldehyde/terpene | 168.24 |
| 5989-27-5 | limonene | citric | terpene | 136.23 |
| 126-91-0 | linalool | lavender/bergamot | terpene | 154.25 |
| 55066-48-3 | mefrosol | flora l/rose | alcohol | 178.27 |
| 2216-51-5 | menthol | peppermint | alcohol | 156.26 |
| 623-42-7 | methyl butyrate | apple/pineapple | ester | 102.13 |
| 123-35-3 | myrcene | herbal/woody | terpene | 136.24 |
| 80-56-8 | pinene | pine | terpene | 136.24 |
| 357650-26-1 | pomarose | plums/apples rose | ketone | 166.26 |
| 89-82-7 | pulegone | peppermint | ketone/terpene | 152.24 |
| 65113-99-7 | sandalore | sandalwood | alcohol | 210.36 |
| 121-33-5 | vanilin | vanilla | aldehyde/aromatic | 152.15 |

In an embodiment, the release of the active agent occurs during 30 seconds to 24 h.

In an embodiment, electrolyte solution has a pH between 4.0-8.5. In a further embodiment, the electrolyte solution is sweat, salty water or micellar water, preferably human sweat or pet sweat.

In an embodiment, the unmodified protein is stable in polar and non-polar solvents, including methanol, butanol, benzene, ethanol and undecanol as well as buffer solutions, preferably Tris-HCl, phosphate, or phosphate buffered saline (PBS)). In a further embodiment, the unmodified protein is also stable in temperatures between 18-70° C., preferably 18-60° C., and in a pH range of 4.0-10.0.

In an embodiment, the protein is stable in polar and non-polar solvents, including methanol, butanol, benzene and undecanol as well as buffer solutions (Tris-HCl, phosphate, PBS). In a further embodiment, the protein is also stable in temperatures between 18-70° C., preferably 18-60° C., and in a pH range of 4.0-10.0.

In an embodiment, the release of the active agent from the protein occurs at 20-40° C.

In an embodiment, the composition further comprises glycerol, erythritol, arabitol, sorbitol, mannitol, xylitol, mannisdomannitol, glucosylglycerol, glucose, fructose, sucrose, trehalose, isofluoroside, dextrans, levans, polyethylene glycol, salts of chloride, citrate, sulfates, acetate or phosphates, or mixtures thereof.

An aspect of the present disclosure comprises a kit or article comprising the composition described in the present subject-matter. In an embodiment, the article comprising said composition can be selected from a list comprising fabric, textiles, fibers, clothes, scarfs, hats, gloves, socks and turbans, shoes, insoles, bags, handbags, detergents, creams, lotions, foams, perfumes, softeners, aerosols, deodorants, lipsticks, lip creams, face mask powders, face and body creams, skin clarifiers, primers, foundations, hair shampoos, hair serum, hairs masks, hair conditioners or hair coloration creams.

The present disclosure also relates to the use of the fragrance release composition described in the present subject-matter in cosmetics, preferably as a cosmetic agent/composition, more preferably skin care or hair care; as well as the use of said composition in the textile industry.

The present disclosure also relates to the use of the fragrance release composition as a deodorant agent/composition.

BRIEF DESCRIPTION OF THE DRAWINGS

The following FIGURES provide preferred embodiments for illustrating the disclosure and should not be seen as limiting the scope of invention.

FIG. 1: Schematic representation Sodium dodecyl sulfate and polyacrylamide (SDS-PAGE) gel electrophoresis under reducing conditions (A), and circular dichroism (CD) spectrum (B) of native pig odorant-binding protein. Mw: Precision Plus Protein™ standards (BioRad).

DETAILED DESCRIPTION

The present disclosure concerns the method of manufacture of a fragrance/protein complex and the adsorption and dissociation mechanism of native odorant-binding protein (OBP-I), in particular pig OBP-I, and native protein fused with $GQ_{20}$ and KP peptide. This mechanism involves the release of active agents, preferably odorific molecules (or fragrances), in response to human perspiration.

The present disclosure presents high impact in textile and cosmetic fields, particularly in the release of fragrances from lotion and cream base products as well as textile fabrics, awarding a green solution.

In an embodiment, the produced odorant-binding protein and fragrance/protein complex are very soluble and stable at different solvents (like methanol, butanol, benzene and undecanol) and different range of temperature (18-60° C.) and different range of pH (4.0-10.0).[12, 27-29]

In a further embodiment, the mixture of odorific molecules and the OBP-I or OBP::$GQ_{20}$::KP proteins showed improved results regarding the affinity constants in a buffer solution and in sweat (Table 2). In particular, the lower Ka in sweat enforces the use of OBP proteins when sweat-triggered responses are envisaged. Notably, the adsorption and dissociation mechanism by the proteins is reversible. In response to human perspiration at different range of pH (pH 4.0-8.5) the disclosed proteins released more than 20× to 6.8× (OBP-I and OBP::$GQ_{20}$::KP, respectively) of odorific molecules compared with other fusion proteins based on porcine odorant-binding protein (Table 2). Thus, the release of fragrance occurs in response of perspiration and it is independent of pH of sweat of each human. Additionally, the fragrance release occurs at least during 0.5-24 h.

In an embodiment, a variety of active agents, including deodorizing agents, natural essences, fragrance agents, moisturizing agents, or mixtures thereof, can be used in the complex formation, allowing a wide range of cosmetic uses. In particular, pleasant odorific molecules (of different size and shape) showed great affinity to the odorant-binding protein, in particular porcine odorant-binding protein.

In an embodiment, the odorific molecules used in the present disclosure belong to different functional groups (aromatic, aldehyde, alcohols). In a further embodiment the odorific molecules comprise molecules with a molecular weight ranging from 20.00 to 1000.00 g/mol, and the concentration varies from 0.2-2000 μM.

In an embodiment, odorific molecules have a molecular weight between 75 to 300 g/mol.

In an embodiment, the system efficiently responded to human perspiration, releasing fragrances over time. Importantly, the system did not respond against the water existent in human body, giving specificity and robustness to the subject-matter presented in this disclosure. Without this selectivity, i.e., if the system responded to water, the OBP protein would immediately release the odorific molecules when in contact with the skin.

EXAMPLE

In an embodiment, native porcine odorant-binding protein (OBP-I) and OBP-I fused with a spacer glycine-glutamine, repeated 20× (GQ$_{20}$) and with a carbohydrate-binding module (OBP::GQ$_{20}$::CBM) were cloned in plasmid pET28a and transformed into *Escherichia coli* BL21(DE3). The proteins were expressed and purified through Nickel magnetic beads with specificity to His-tag present in the protein's N-terminal. 10 μM of protein were loaded on sodium dodecyl sulfate and polyacrylamide (SDS-PAGE) gel electrophoresis under reducing conditions. The same concentration was used to determine the structure of proteins by circular dichroism (CD) spectroscopy.

The protein purified in laboratory reveals a high level of purity (observed by SDS-PAGE gel, FIG. 1-A) and secondary structure in barrel, a consequence of the presence of a high number of β-sheets, as analysed by circular dichroism spectroscopy (FIG. 1-B).

In an embodiment, the pure odorant-binding protein was lyophilized and used in further procedures. To determine the affinity of the odorant-binding protein to odour molecules, 1-aminoanthracene (1-AMA) was used as an odour model molecule. Increased concentrations of fluorescent ligand model 1-aminoanthracene (1-AMA) were added to 1 μM of protein, and the formation of ligand/protein complex was quantified after 1 h at 37° C. by fluorescence emission at 481 nm (excitation at 295 nm).[30] Dissociation constant (Kd) was determined from a plot of fluorescence intensity versus concentration of ligand, obtained with a standard non-linear regression method, described in Malpeli et al. (1998).[31] The affinity behaviour of protein in presence of sweat solution was performed through a competitive fluorescence assay. Here, 1 μM of protein was mixed with 2 μM of 1-AMA and incubated at 37° C. for 1 h. After this period, increased volumes of sweat solution were added to the complex and incubated at same conditions.

In an embodiment, the sweat solution was prepared as indicated in AATCC method 15-2009 "Colorfastness to Perspiration". The pH of the prepared solution varied between 4.0 and 8.5. In accordance with its composition, the sweat solution is also regarded as electrolyte solution.

In a further embodiment, fluorescence emission at 481 nm (excitation at 295 nm) was recorded and the dissociation constant (Kd) calculated. The association constant (Ka) was calculated by formula Kd=1/Ka.

In an embodiment, the release of fragrance was quantified by gas chromatography-mass spectrometry (GC-MS). Increased concentrations of fragrance were used in different vials and the fragrance in headspace quantified performing the calibration curve (area of peak vs fragrance concentration). The fragrance was incubated with the odorant-binding protein at 37° C. Sweat solution was added and the fragrance release determined after several periods of time (0.5-24 h) of perspiration exposition.

In an embodiment, as comparative data, porcine odorant-binding protein was fused with a spacer GQ$_{20}$ and a carbohydrate-binding module (CBM), as previously reported.[25] Through the fusion of CBM$_{N1}$ (PDB ID 1ULP) of endoglucanase C from *Cellulomonas fimi*, the OBP has a specific affinity to cotton. The modified protein showed a high association constant (Ka=4.17±0.05 μM) that decreased for Ka=3.16±0.02 μM when a sweat solution was added. Native OBP-I (SEQ ID No. 1) and OBP::GQ$_{20}$::KP (SEQ ID NO. 21) showed an association constant very similar (Ka=4.00±0.03 μM) to the value obtained for OBP::GQ$_{20}$::CBM (SEQ ID NO. 22, Ka=4.17±0.05). However, the addition of the sweat solution had a remarkable effect on constant of affinity of the native protein (Ka=0.20±0.02 μM) and of the OBP::GQ$_{20}$::KP (Ka=0.59±0.01 μM). A high reduction of affinity was observed, 20× using native OBP (SEQ ID NO. 1) and 6.8× using OBP::GQ$_{20}$::KP (SEQ ID NO. 21), as compared with the value quantified for protein fused with CBM (SEQ ID NO 22), where a reduction of only 1.3× was verified (Ka=3.16±0.02 Table 2). Thus, the release of fragrance by OBP-I and OBP fused with KP is evident in response of perspiration.

TABLE 2

Affinity constant (Ka) of native OBP-I (SEQ ID NO. 1) and fusion proteins based on OBP, SEQ ID NO. 21 and SEQ ID NO 22. SEQ ID NO 22 was used as comparative data. Values are the mean of 2 independent experiments at 37° C.

| Protein | Ka in buffer (μM) | Ka in sweat (μM) |
|---|---|---|
| Native porcine OBP (OBP-I) - SEQ ID NO 1 | 4.00 ± 0.03 | 0.20 ± 0.02 |
| OBP::GQ$_{20}$::KP - SEQ ID NO 21 | 4.00 ± 0.04 | 0.59 ± 0.01 |
| OBP::GQ$_{20}$::CBM (fusion protein)[25] - SEQ ID NO 22 | 4.17 ± 0.05 | 3.16 ± 0.02 |

In an embodiment, the following protein sequences can be incorporated in different substrates in order to release fragrances in the presence of sweat. In this regard, substrates can be selected from a list comprising textiles, fabrics, skin care products, hair care products, among others.

LIST OF PROTEIN SEQUENCES

The sequences of protein are described by one letter code of amino acids. The code is as follows:

| One letter code | Amino acid |
|---|---|
| A | Alanine |
| C | Cysteine |
| D | Aspartic acid |
| E | Glutamic acid |
| F | Phenylalanine |
| G | Glycine |

-continued

-continued

| One letter code | Amino acid |
| --- | --- |
| H | Histidine |
| I | Isoleucine |
| K | Lysine |
| L | Leucine |
| M | Methionine |
| N | Asparagine |
| P | Proline |
| Q | Glutamine |

| One letter code | Amino acid |
| --- | --- |
| R | Arginine |
| S | Serine |
| T | Threonine |
| V | Valine |
| W | Tryptophan |
| Y | Tyrosine |

Pig OBP (PDB ID 1DZK)-
SEQ ID NO. 1
QEPQPEQDPFELSGKWITSYIGSSDLEKIGENAPFQVFMRSIEFDDKESKVYLNFFSKENGICEEFSLI

GTKQEGNTYDVNYAGNNKFVVSYASETALIISNINVDEEGDKTIMTGLLGKGTDIEDQDLEKFKEVT

RENGIPEENIVNIIERDDCPA

Human OBP$_{IIa}$ (UniProt ID Q9NY56)-
SEQ ID NO. 2
MKTLFLGVTLGLAAALSFTLEEEDITGTWYVKAMVVDKDFPEDRRPRKVSPVKVTALGGGNLEATF

TFMREDRCIQKKILMRKTEEPGKFSAYGGRKLIYLQELPGTDDYVFYCKDQRRGGLRYMGKLVGR

NPNTNLEALEEFKKLVQHKGLSEEDIFMPLQTGSCVLEH

Human OBPIIb (UniProt ID Q9NPH6)-
SEQ ID NO. 3
MKTLFLGVTLGLAAALSFTLEEEDITGTWYVKAMVVDKDFPEDRRPRKVSPVKVTALGGGKLEATF

TFMREDRCIQKKILMRKTEEPGKYSAYGGRKLMYLQELPRRDHYIFYCKDQHHGGLLHMGKLVGR

NSDTNREALEEFKKLVQRKGLSEEDIFTPLQTGSCVPEH

Mouse OBP (UniProt ID OBP1A)
SEQ ID NO. 4
MAKFLLLALTFGLAHAAMEGPWKTVAIAADRVDKIERGGELRIYCRSLTCEKECKEMKVTFYVNEN

GQCSLTTITGYLQEDGKTYKTQFQGNNRYKLVDESPENLTFYSENVDRADRKTKLLFILGHGPLTSE

QKEKFAELAEEKGIPAGNIREVLITDYCPE

Mouse OBP2A (UniProt ID Q8K1H9)-
SEQ ID NO. 5
MKSLLLTILLLGLVAVLKAQEAPPDDLVDYSGIWYAKAMVHNGTLPSHKIPSIVFPVRIIALEEGDLE

TTVVFWNNGHCREFKFVMKKTEEPGKYTAFHNTKVIHVEKTSVNEHYIFYCEGRHNGTSSFGMG

KLMGRDSGENPEAMEEFKNFIKRMNLRLENMFVPEIGDKCVESD

Mouse OBP1B (UniProt ID A2AEP0)-
SEQ ID NO. 6
MMVKFLLLALVFGLAHVHAHDHPELQGQWKTTAIMADNIDKIETSGPLELFVREITCDEGCQKM

KVTFYVKQNGQCSLTTVTGYKQEDGKTFKNQYEGENNYKLLKATSENLVFYDENVDRASRKTKLLY

ILGKGEALTHEQKERLTELATQKGIPAGNLRELAHEDTCPE

Rat OBP (PDB ID 3FIQ)-
SEQ ID NO. 7
HHENLDISPSEVNGDWRTLYIVADNVEKVAEGGSLRAYFQHMECGDECQELKIIFNVKLDSECQT

HTVVGQKHEDGRYTTDYSGRNYFHVLKKTDDIIFFHNVNVDESGKETNVILVAGKREDLNKAQKQ

ELRKLAEEYNIPNENTQHLVPTDTCNQ

Rat OBP (PDB ID 3ZQ3)-
SEQ ID NO. 8
MRGSHHHHHHTDPEEASFERGNLDVDKLNGDWFSIVVASDKREKIEENGSMRVFVQHIDVLENS

LGFTFRIKENGVCTEFSLVADKTAKDGEYFVEYDGENTFTILKTDYDNYVMFHLVNVNNGETFQLM

ELYGRTKDLSSDIKEKFAKLCVAHGITRDNIIDLTKTDRCLQA

Rat OBP (UniProt ID P08937)-

SEQ ID NO. 9

MVKFLLIVLALGVSCAHHENLDISPSEVNGDWRTLYIVADNVEKVAEGGSLRAYFQHMECGDECQ

ELKIIFNVKLDSECQTHTVVGQKHEDGRYTTDYSGRNYFHVLKKTDDIIFFHNVNVDESGRRQCDL

VAGKREDLNKAQKQELRKLAEEYNIPNENTQHLVPTDTCNQ

Bovine OBP (PDB ID 1OBP)-

SEQ ID NO. 10

AQEEEAEQNLSELSGPWRTVYIGSTNPEKIQENGPFRTYFRELVFDDEKGTVDFYFSVKRDGKWK

NVHVKATKQDDGTYVADYEGQNVFKIVSLSRTHLVAHNINVDKHGQTTELTGLFVKLNVEDEDLE

KFWKLTEDKGIDKKNVVNFLENEDHPHPE

Boar OBP (PDB ID 1GM6)-

SEQ ID NO. 11

HKEAGQDVVTSNFDASKIAGEWYSILLASDAKENIEENGSMRVFVEHIRVLDNSSLAFKFQRKVNG

ECTDFYAVCDKVGDGVYTVAYYGENKFRLLEVNYSDYVILHLVDVNGDKTFQLMEFYGRKPDVEP

KLKDKFVEICQQYGIIKENIIDLTKIDRCFQLRGSGGVQESSAE

Panda OBP (PDB ID 5NGH)-

SEQ ID NO. 12

HEEGNDVRRNFDVSKISGYWYSVLLASDVREKTEENSSMRVFVNHIEVLSNSSLLFNMHIKVDGKC

TEIALVSDKTEKDGEYSVEYDGYNVFRIVETDYTDYIIFHLVNFKEKDSFQMMELSAREPDTSEEVRK

RFVEYCQKHGIVKENIFDLTEVDRCLQARGSEKA

Chinese hamster OBP (Ensembl ID ENSCGRP00015014591.1)-

SEQ ID NO. 13

MVKFLLLAFALSVSCAHHKIPEISPSEVDGKWRTLYIGADNTEKVIQGGPLRAYFRHMECSDECQTL

TITFNTKEEGKCQTHTVVGRKDEDGQYKTGFSGNNDFHVVEKADGIIIFHNVNVDSSGKKTNVILV

AGKGKSLSKEQKERLENIAKEFDISKENIQHLVPTDTCDQ

Meishan pig OBP (Ensembl ID ENSSSCP00040041163.1)-

SEQ ID NO. 14

MKSLLLSLVLGLVCAQEPQPEQDPFVLSGKWITSYIGSSDLEKIGENAPFQVFMRSIEFDDKESKVYL

NFFSKENGICEEFSLIGTKQEGNTYDVNYAGNNKFVVSYASETALIISNINVDEEGDKTIMTGLLGKG

TDIEDQDLEKFKEVTRENGIPEENIVNIIERDDCPAK

Horse OBP (Ensembl ID ENSECAP00000000103.2)-

SEQ ID NO. 15

MQILLLSLVLGVVCAVQEPQSETDYSLFSGEWNTIYIGSSNIEKISENGPFRILLRRLDLDSAGDRIIYT

FFLKVNGQCTKISSLAIKTEENTYVCHYAGKNKFEILHLSKTAIIIDIVNEDEGGLVTKMVALVGMLG

DIQKEDIEKFKEVAKEKEIPEENIVNIINIDDCPTSE

Guinea pig OBP ((Ensembl ID ENSCPOP00000016393.2)-

SEQ ID NO. 16

MQILLLALTIGLAYAHQTLDPSEINGQWHTISIAADNVEKIGEGGPLRGYFHNLHCYDGCKNIGLTF

YVKLDGNCQRFDVLGAKQEDSDVYVAQYSGTNHFEVIGKKEDAIAFYNHNTDETGKETKMIVVVA

RRDSLTEEEQQKLQEVAGEKGIPKDNIRYFRERDTCAQ

Dog OBP ((Ensembl ID ENSCAFP00040020992.1)-

SEQ ID NO. 17

MKILLLCLILVLACDAHLPLPNVLTQVSGPWKTLYVSSNNLDKIAENGPFRIYIRRINVDIPRLKILFSF

FVKVDGECVEKSVEASIGQDNLINAHYAGGNYHQILDVTPNALIGYIVNVDDKGRITKLASLVGRG

AHVNEEDIAKFKKLSREKGIPEENIIYLGDTDNCPNHE

Tibetan pig OBP (Ensembl ID ENSSSCP00015013912.1)-

SEQ ID NO. 18

MKSLLLSLVLGLVCAQEPQPEQDPFELSGKWITSYIGSSDLEKIGENAPFQVFMRSIEFDDKESKVYL

NFFSKENGICEEFSLTGTKQEGNTYDVNYAGNNKFVVSYASETALIIANINVDEEGDKTIMTGLLGK

GTDIEDQDLEKFKEVTRENGIPEENIVNIIERDDCPAK

-continued

Cat felis OBP (Ensembl ID ENSFCAP00000053707.1)-
SEQ ID NO. 19
RSCVIHLQCLPTGCLFSALHNGLPDGRLPLPDGRLPLPDGRLPLPDSRLPLPDGRLPLPDGRLPLPDG

RLPLPDGRLPLPDGRLPLPDGRLPLPDGRLPLPDGRLPLPEGRLPLPDSHPPLQDNLTQLSGEWNTL

LVAATNVDKISNGPFHGYICKVDVDVTNGTVVFNFSVMMNGRCTEKSAVGTIGRDKFINIGSMN

QNLFNLFSVTSNTIAINVNTRRNTTKAFALLDTNGNIFNIGYDSLGSLIIHTANVDTAGQTTQVFALL

GKRLHPDDNDFAKFRELMRENNIPEENLIDMSKTEKCPKKEKGTNPS

Chimpanzee OBP (Ensembl ID ENSPTRP00000048681.3)-
SEQ ID NO. 20
MALLLLSLGLSLITAQEFDPRNVMQRNYNMARVSGVWYSIFMADDLNRIKENGDLRVFVQNIEHL

KNGSLKFDFEYMVQGECVAVVVVCEKTEKNGEYSINYEGQNTVAVSETDYRLFITFHLQNFRNGTE

THTLALYETCKKYGLGSQNIINLTNKDPCYSKHYRSPPRPPMRE

OBP::GQ$_{20}$::KP (recombinant protein)-
SEQ ID NO. 21
QEPQPEQDPFELSGKWITSYIGSSDLEKIGENAPFQVFMRSIEFDDKESKVYLNFFSKENGICEEFSLI

GTKQEGNTYDVNYAGNNKFVVSYASETALIISNINVDEEGDKTIMTGLLGKGTDIEDQDLEKFKEVT

RENGIPEENIVNIIERDDCPAGQGQGQGQGQGQGQGQGQGQGQGQGQGQGQGQGQGQGQGQGQGQGQ

GQGGVCGPSPPCITT

OBP::GQ$_{20}$::CBM (recombinant protein)-
SEQ ID NO. 22
QEPQPEQDPFELSGKWITSYIGSSDLEKIGENAPFQVFMRSIEFDDKESKVYLNFFSKENGICEEFSLI

GTKQEGNTYDVNYAGNNKFVVSYASETALIISNINVDEEGDKTIMTGLLGKGTDIEDQDLEKFKEVT

RENGIPEENIVNIIERDDCPAGQGQGQGQGQGQGQGQGQGQGQGQGQGQGQGQGQGQGQGQGQGQGQ

GQASPIGEGTFDDGPEGWVAYGTDGPLDTSTGALCVAVPAGSAQYGVGVVLNGVAIEEGTTYTL

RYTATASTDVTVRALVGQNGAPYGTVLDTSPALTSEPRQVTETFTASATYPATPAADDPEGQIAFQ

LGGFSADAWTLCLDDVALDSEVEL

REFERENCES (1) Flower, D. R. The lipocalin protein family: structure and function. Biochem. J. 1996, 318, 1-14.

(2) Flower, D. R. Beyond the superfamily: the lipocalin receptors. Biochimica et biophysica acta 2000, 1482, 327-336.

(3) Breer, H. Olfactory receptors: molecular basis for recognition and discrimination of odors. Analytical and bioanalytical chemistry 2003, 377 (3), 427-33, DOI: 10.1007/s00216-003-2113-9.

(4) Tegoni, M.; Pelosi, P.; Vincent, F.; Spinelli, S.; Campanacci, V.; Grolli, S.; Ramoni, R.; Cambillau, C. Mammalian odorant binding proteins. Biochimica et biophysica acta 2000, 1482, 229-240.

(5) Bignetti, E.; Cattaneo, P.; Cavaggioni, A.; Damiani, G. The pyrazine-binding protein and olfaction. Comp. Biochem. Physiol. 1988, 90B, 1-5.

(6) Pevsner, J.; Hou, V.; Snowman, A. M.; Snyder, S. H. Odorant-binding protein: characterization of ligand binding. The Journal of biological chemistry 1990, 265 (11), 6118-6125.

(7) Bignetti, E.; Cavaggioni, A.; Pelosi, P.; Persaud, K. C.; Sorbi, R. T.; Tirindelli, R. Purification and characterisation of an odorant-binding protein from cow nasal tissue. Eur. J. Biochem. 1985, 149, 227-231.

(8) Dal Monte, M.; Andreini, I.; Revoltella, R.; Pelosi, P. Purification and characterization of two odorant-binding proteins from nasal tisue of rabbit and pig. Comp Biochem Physiol 1991, 99B (2), 445-451.

(9) Garibotti, M.; Navarrini, A.; Pisanelli, A. M.; Pelosi, P. Three Odorant-binding Proteins from Rabbit Nasal Mucosa. Chemical senses 1997, 22 (4), 383-390.

(10) Lazar, J.; Greenwood, D. R.; Rasmussen, L. E. L; Prestwich, G. D. Molecular and Functional Characterization of an Odorant Binding Protein of the Asian Elephant, *Elephas maximus*: Implications for the Role of Lipocalins in Mammalian Olfaction. Biochemistry 2002, 41, 11786-11794.

(11) Pes, D.; Dal Monte, M.; Ganni, M.; Pelosi, P. Isolation of two odorant-binding proteins from mouse nasal tissue. Comp. Biochem. Physiol. 1992, 103B (4), 1011-1017.

(12) Lobel, D.; Jacob, M.; Volkner, M.; Breer, H. Odorant of different chemica classes interact with distinct odorant binding protein subtypes. Chemical senses 2002, 27, 39-44.

(13) Briand, L.; Eloit, C.; Nespoulous, C.; Bezirard, V.; Huet, J.-C.; Henry, C.; Blon, F.; Trotier, D.; Permollet, J.-C. Evidence of an Odorant-Binding Protein in the Human Olfactory Mucus: Location, Structural Characterization, and Odorant-Binding Properties. Biochemistry 2002, 41, 7241-7252.

(14) Pelosi, P. Odorant-Binding Proteins: Structural Aspects. In Annals New York academy of sciences; Olfaction and Taste XII: an international symposium, 1998; pp 281-293.

(15) Spinelli, S.; Ramoni, R.; Grolli, S.; Bonicel, J.; Cambillau, C.; Tegoni, M. The Structure of the Monomeric Porcine Odorant Binding Protein Sheds Light on the Domain Swapping Mechanism. Biochemistry 1998, 37, 7913-7918.

17 18

(16) Perduca, M.; Mancia, F.; Del Giorgio, R.; Monaco, H. L. Crystal Structure of a Truncated Formof Porcine Odorant-Binding Protein. Proteins: Structure, Function, and Genetics 2001, 42, 201-209.

(17) Cave, J. W.; Wickiser, J. K.; Mitropoulos, A. N. Progress in the development of olfactory-based bioelectronic chemosensors. Biosensors & bioelectronics 2019, 123, 211-222, DOI: 10.1016/j.bios.2018.08.063.

(18) Pelosi, P.; Mastrogiacomo, R.; Iovinella, I.; Tuccori, E.; Persaud, K. C. Structure and biotechnological applications of odorant-binding proteins. Applied microbiology and biotechnology 2014, 98 (1), 61-70, DOI: 10.1007/s00253-013-5383-y.

(19) Mulla, M. Y.; Tuccori, E.; Magliulo, M.; Lattanzi, G.; Palazzo, G.; Persaud, K.; Torsi, L. Capacitance-modulated transistor detects odorant binding protein chiral interactions. Nature communications 2015, 6, 6010, DOI: 10.1038/ncomms7010.

(20) Paolini, S.; Tanfani, F.; Fini, C.; Bertoli, E.; Pelosi, P. Porcine odorant-binding protein: structural stability and ligand afinities measured by Fourier-transform infrared spectroscopy and fluorescence spectroscopy. Biochimica et biophysica acta 1999, 1431, 179-188.

(21) Sorokowska, A.; Sorokowski, P.; Szmajke, A. Does Personality Smell? Accuracy of Personality Assessments Based on Body Odour. European Journal of Personality 2012, 26 (5), 496-503, DOI: 10.1002/per.848.

(22) Ozeki, C.; Moro, O. A study of the suppression of body odour in elderly subjects by anti-fungal agents. International journal of cosmetic science 2016, 38 (3), 312-8, DOI: 10.1111/ics.12295.

(23) Di Pietrantonio, F.; Cannata, D.; Benetti, M.; Verona, E.; Varriale, A.; Staiano, M.; D'Auria, S. Detection of odorant molecules via surface acoustic wave biosensor array based on odorant-binding proteins. Biosensors & bioelectronics 2013, 41, 328-34, DOI: 10.1016/j.bios.2012.08.046.

(24) Sankaran, S.; Khot, L. R.; Panigrahi, S. Biology and applications of olfactory sensing system: A review. Sensors and Actuators B: Chemical 2012, 171-172, 1-17, DOI: 10.1016/j.snb.2012.03.029.

(25) Goncalves, F.; Ribeiro, A.; Silva, C.; Cavaco-Paulo, A. Release of Fragrances from Cotton Functionalized with Carbohydrate-Binding Module Proteins. ACS Appl Mater Interfaces 2019, DOI: 10.1021/acsami.9b08191.

(26) Kozlowski, L. P. IPC—Isoelectric Point Calculator. Biology direct 2016, 11(1), 55, DOI: 10.1186/s13062-016-0159-9.

(27) Cennamo, N.; Di Giovanni, S.; Varriale, A.; Staiano, M.; Di Pietrantonio, F.; Notargiacomo, A.; Zeni, L.; D'Auria, S. Easy to Use Plastic Optical Fiber-Based Biosensor for Detection of Butanal. PloS one 2015, 10 (3), e0116770, DOI: 10.1371/journal.pone.0116770.

(28) Capo, A.; Pennacchio, A.; Varriale, A.; D'Auria, S.; Staiano, M. The porcine odorant-binding protein as molecular probe for benzene detection. PloS one 2018, 13 (9), e0202630, DOI: 10.1371/journal.pone.0202630.

(29) Vincent, F.; Ramoni, R.; Spinelli, S.; Grolli, S.; Tegoni, M.; Cambillau, C. Crystal structures of bovine odorant-binding protein in complex with odorant molecules. European journal of biochemistry 2004, 271 (19), 3832-42, DOI: 10.1111/j.1432-1033.2004.04315.x.

(30) Goncalves, F.; Castro, T. G.; Nogueira, E.; Pires, R.; Silva, C.; Ribeiro, A.; Cavaco-Paulo, A. OBP fused with cell-penetrating peptides promotes liposomal transduction. Colloids and surfaces. B, Biointerfaces 2018, 161, 645-653, DOI: 10.1016/j.colsurfb.2017.11.026.

(31) Malpeli, G.; Folli, C.; Cavazzini, D.; Sartori, G.; Berti, R. Purification and Fluorescent Titration of Cellular Retinol-Binding Protein. In Methods in Molecular Biology; Redfern, C. P. F., Ed.; 1998; pp 111-122.

(32) Nogueira, E.; Mangialavori, I. C.; Loureiro, A.; Azoia, N. G.; Sárria, M. P.; Nogueira, P.; Freitas, J.; Harmark, J.; Shimanovich, U.; Rollet, A.; Lacroix, G.; Bernardes, G. J. L.; Guebitz, G.; Hebert, H.; Moreira, A.; Carmo, A. M.; Rossi, J. P. F. C.; Gomes, A. C.; Preto, A.; Cavaco-Paulo, A. Peptide anchor for folate-targeted liposomal delivery. Biomacromolecules 2015, 16 (9), 2904-2910, DOI: 10.1021/acs.biomac.5b00823.

(33) Gonçalves, F.; Silva, C.; Ribeiro, A.; Cavaco-Paulo, A. 1-Aminoanthracene Transduction into Liposomes Driven by Odorant-Binding Protein Proximity. ACS Applied Materials & Interfaces 2018, DOI: 10.1021/acsami.8b10158.

(34) Goncalves, F.; Castro, T. G.; Azoia, N. G.; Ribeiro, A.; Silva, C.; Cavaco-Paulo, A. Two Engineered OBPs with opposite temperature-dependent affinities towards 1-aminoanthracene. Scientific reports 2018, 8 (1), 14844, DOI: 10.1038/s41598-018-33085-8.

The term "comprising" whenever used in this document is intended to indicate the presence of stated features, integers, steps, components, but not to preclude the presence or addition of one or more other features, integers, steps, components or groups thereof.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

The invention claimed is:

1. A composition comprising:

0.01 to 5000 μM of an odorant binding protein comprising an amino acid sequence of SEQ ID NO: 21; and 0.1 μM to 2 M of an active agent, wherein the active agent is a deodorizing agent, a natural essence, a fragrance, a moisturizing agent, or a combination of two or more thereof, wherein the active agent is released from the odorant binding protein in the presence of an electrolyte solution at a temperature of about 10° C. to about 70° C., wherein the active agent has a molecular weight from 20 to 1000 g/mol, and wherein the electrolyte solution comprises sweat, salty water or micellar water.

2. The composition according to claim 1, wherein the active agent is present at a concentration of about 0.2 μM to about 1 M.

3. The composition according to claim 1, wherein the odorant binding protein has an affinity constant to the active agent in water or a buffer solution of about 1 μM to about 4.5 μM.

4. The composition according to claim 1, wherein the odorant binding protein has an affinity constant to the active agent in an electrolyte solution of about 0.1 μM to about 0.99 μM.

5. The composition according to claim 1, wherein the active agent has a molecular weight from 75-300 g/mol.

6. The composition according to claim 1, wherein the active agent is a fragrance molecule.

7. The composition according to claim 1, wherein the active agent is a fragrance molecule comprising 2-acetyl-1-pyrroline, α-terpineol, β-ocimene, benzyl acetate, butyl acetate, camphor, carvone, citral, citronellol, coumarin, diacetyl, eugenol, fructone, gamma decalactone, gamma nonalactone, geraniol, hedione, isoamyl acetate, lilac aldehyde, limonene, linalool, mefrosol, menthol, methyl butyrate, myrcene, pinene, pomarose, pulegone, sandalore, vanillin, or a combination of two or more thereof.

8. The composition according to claim 1, wherein the active agent is released over about 30 seconds to about 24 hours.

9. The composition according to claim 1, wherein the odorant binding protein is stable in polar and non-polar solvents, wherein the polar and non-polar solvents comprise ethanol, methanol, butanol, benzene and undecanol.

10. The composition according to claim 1, wherein the odorant binding protein is stable at temperatures of about 18° C. to about 70° C.

11. The composition according to claim 1, wherein the odorant binding protein is stable in a pH range of about 4.0 to about 10.0.

12. The composition according to claim 1, further comprising glycerol, erythritol, arabitol, sorbitol, mannitol, xylitol, mannitol, glucosylglycerol, glucose, fructose, sucrose, trehalose, isofluoroside, dextrans, levans, polyethylene glycol, salts of chloride, citrate, sulfates, acetate, or phosphates, or a combination of two or more thereof.

13. The composition according to claim 1, wherein the composition is used as a cosmetic composition.

14. The composition according to claim 13, wherein the composition is used as a deodorant composition.

15. A kit or article comprising the composition according to claim 1.

16. The kit or article according to claim 15, wherein the article is selected from the group consisting of fabric, textiles, fibers, clothes, scarfs, hats, gloves, socks and turbans, shoes, insoles, bags, handbags, detergents, creams, lotions, foams, perfumes, softeners, aerosols, deodorants, lipsticks, lip creams, face mask powders, face and body creams, skin clarifiers, primers, foundations, eyelash mascaras, hair shampoos, hair serum, hairs masks, hair conditioners or hair coloration creams.

* * * * *